(12) United States Patent
Schmidt et al.

(10) Patent No.: US 12,403,306 B2
(45) Date of Patent: Sep. 2, 2025

(54) ELECTRIC FIELD SHAPING LEADS FOR TREATMENT OF CANCER

(71) Applicant: Cardiac Pacemakers, Inc., St. Paul, MN (US)

(72) Inventors: Brian L. Schmidt, White Bear Lake, MN (US); Jacob M. Ludwig, Isanti, MN (US); Benjamin J. Haasl, Forest Lake, MN (US); Michael J. Kane, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/167,079

(22) Filed: Oct. 22, 2018

(65) Prior Publication Data

US 2019/0117970 A1 Apr. 25, 2019

Related U.S. Application Data

(60) Provisional application No. 62/575,687, filed on Oct. 23, 2017.

(51) Int. Cl.
 *A61N 1/36* (2006.01)
 *A61B 18/14* (2006.01)
 (Continued)

(52) U.S. Cl.
 CPC .......... *A61N 1/36002* (2017.08); *A61B 18/14* (2013.01); *A61B 18/18* (2013.01);
 (Continued)

(58) Field of Classification Search
 CPC ............. A61N 1/36002; A61N 1/0424; A61N 1/37247; A61N 1/05; A61N 1/36031;
 (Continued)

(56) References Cited

U.S. PATENT DOCUMENTS 4,016,886 A 4/1977 Doss et al.
5,099,838 A 3/1992 Bardy
(Continued)

FOREIGN PATENT DOCUMENTS

AU 2005301103 5/2006
CN 101693875 4/2010
(Continued)

OTHER PUBLICATIONS

International Search Report and Written Opinion for PCT Application No. PCT/US2018/057117 mailed Dec. 20, 2018 (14 pages).
(Continued)

*Primary Examiner* — Mallika D Fairchild
(74) *Attorney, Agent, or Firm* — Pauly, DeVries Smith & Deffner LLC

(57) ABSTRACT

Embodiments herein relate to medical devices including electric field shaping leads and methods for using the same to treat cancerous tumors within a bodily tissue. In an embodiment, an implantable lead for a cancer treatment system is disclosed. The lead can include a lead body having a proximal end and a distal end, where the lead body can define a lumen. The lead can also include a paddle disposed at the distal end of the lead body, the paddle having a width that is greater than a width of the lead body. The paddle can include one or more electrodes disposed on the paddle and one or more electrical conductors disposed within the lumen of the lead body to provide electrical communication between the one or more electrodes and the proximal end of the lead body. Other embodiments are also included herein.

19 Claims, 11 Drawing Sheets

(51) Int. Cl.
   *A61B 18/18* (2006.01)
   *A61N 1/04* (2006.01)
   *A61N 1/05* (2006.01)
   *A61N 1/372* (2006.01)
   *A61N 5/02* (2006.01)

(52) U.S. Cl.
   CPC ............ *A61N 1/0424* (2013.01); *A61N 1/05* (2013.01); *A61N 1/37247* (2013.01); *A61N 5/02* (2013.01); *A61N 1/36031* (2017.08); *A61N 1/37229* (2013.01)

(58) Field of Classification Search
   CPC ...... A61N 1/37229; A61N 5/02; A61B 18/18; A61B 18/14
   USPC .......................................................... 607/2
   See application file for complete search history.

(56) References Cited

U.S. PATENT DOCUMENTS

| | | |
|---|---|---|
| 5,113,869 A | 5/1992 | Nappholz et al. |
| 5,324,328 A | 6/1994 | Li et al. |
| 5,397,342 A | 3/1995 | Heil et al. |
| 5,458,597 A | 10/1995 | Edwards et al. |
| 5,582,609 A | 12/1996 | Swanson et al. |
| 5,630,426 A | 5/1997 | Eggers et al. |
| 5,662,698 A * | 9/1997 | Altman .................. A61N 1/056 607/123 |
| 5,834,051 A | 11/1998 | Woloszko et al. |
| 5,871,530 A | 2/1999 | Williams et al. |
| 6,006,755 A | 12/1999 | Edwards |
| 6,366,808 B1 | 4/2002 | Schroeppel et al. |
| 6,673,623 B1 | 1/2004 | Huberman |
| 6,868,289 B2 | 3/2005 | Palti |
| 6,920,361 B2 | 7/2005 | Williams |
| 7,162,310 B2 | 1/2007 | Doan |
| 7,449,021 B2 | 11/2008 | Underwood et al. |
| 7,524,274 B2 | 4/2009 | Patrick et al. |
| 7,565,205 B2 | 7/2009 | Palti |
| 7,632,235 B1 | 12/2009 | Karicherla et al. |
| 7,656,205 B2 | 2/2010 | Chen et al. |
| 7,715,921 B2 | 5/2010 | Palti |
| 7,720,549 B2 | 5/2010 | Schroeppel et al. |
| 7,805,201 B2 | 9/2010 | Palti |
| 7,809,441 B2 | 10/2010 | Kane et al. |
| 7,890,183 B2 | 2/2011 | Palti et al. |
| 7,917,227 B2 | 3/2011 | Palti |
| 8,002,821 B2 | 8/2011 | Stinson |
| 8,019,414 B2 | 9/2011 | Palti |
| 8,170,648 B2 | 5/2012 | Field et al. |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,262,575 B2 | 9/2012 | Davies |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,483,821 B2 | 7/2013 | Averina et al. |
| 8,500,713 B2 | 8/2013 | Ferek-petric |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 8,805,466 B2 | 8/2014 | Salahieh et al. |
| 8,956,352 B2 | 2/2015 | Mauch et al. |
| 9,005,100 B2 | 4/2015 | Gnanashanmugam et al. |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,179,974 B2 | 11/2015 | Ku et al. |
| 9,248,278 B2 | 2/2016 | Crosby et al. |
| 9,283,383 B2 | 3/2016 | Osypka |
| 9,308,039 B2 | 4/2016 | Azure |
| 9,387,323 B2 | 7/2016 | Fleischhacker et al. |
| 9,427,278 B2 | 8/2016 | Swanson |
| 9,440,068 B2 | 9/2016 | Palti et al. |
| 9,474,486 B2 | 10/2016 | Eliason et al. |
| 9,526,911 B1 | 12/2016 | Azure et al. |
| 9,630,022 B2 | 4/2017 | Bourke et al. |
| 9,655,669 B2 | 5/2017 | Palti et al. |
| 9,717,552 B2 | 8/2017 | Cosman et al. |
| 9,750,934 B2 | 9/2017 | Palti et al. |
| 9,775,671 B2 | 10/2017 | Azure |
| 9,833,617 B2 | 12/2017 | Travers et al. |
| 9,877,781 B2 | 1/2018 | Grasse et al. |
| 9,910,453 B2 | 3/2018 | Wasserman et al. |
| 10,029,117 B2 | 7/2018 | Bourke |
| 10,238,862 B2 | 3/2019 | Cook et al. |
| 10,265,530 B1 | 4/2019 | Perryman et al. |
| 10,376,177 B2 | 8/2019 | Valvano et al. |
| 10,471,254 B2 | 11/2019 | Sano et al. |
| 11,191,956 B2 | 12/2021 | Giladi et al. |
| 11,331,493 B2 | 5/2022 | Pivonka et al. |
| 11,338,135 B2 | 5/2022 | Schmidt et al. |
| 11,420,049 B2 | 8/2022 | Schmidt et al. |
| 11,607,542 B2 | 3/2023 | Schmidt et al. |
| 11,691,006 B2 | 7/2023 | Schmidt et al. |
| 11,712,561 B2 | 8/2023 | Schmidt et al. |
| 11,850,422 B2 | 12/2023 | Schmidt et al. |
| 11,883,655 B2 | 1/2024 | Srivastava et al. |
| 12,109,412 B2 | 10/2024 | Schmidt et al. |
| 12,186,553 B2 | 1/2025 | Schmidt et al. |
| 2001/0044643 A1 | 11/2001 | Litovitz |
| 2002/0026183 A1 | 2/2002 | Simpson |
| 2002/0049485 A1 * | 4/2002 | Smits .................. A61N 1/056 607/122 |
| 2002/0065544 A1 * | 5/2002 | Smits .................. A61N 1/0563 607/122 |
| 2003/0020416 A1 | 1/2003 | Kobayashi |
| 2003/0069623 A1 | 4/2003 | Stypulkowski |
| 2003/0204161 A1 | 10/2003 | Ferek-Petric |
| 2004/0010290 A1 | 1/2004 | Schroeppel et al. |
| 2004/0010303 A1 * | 1/2004 | Bolea .................. A61N 1/36053 607/116 |
| 2004/0147969 A1 | 7/2004 | Mann et al. |
| 2004/0158288 A1 | 8/2004 | Keisari et al. |
| 2004/0162600 A1 | 8/2004 | Williams |
| 2004/0176804 A1 | 9/2004 | Palti |
| 2004/0215235 A1 | 10/2004 | Jackson et al. |
| 2004/0215296 A1 | 10/2004 | Ganz et al. |
| 2005/0004507 A1 | 1/2005 | Schroeppel et al. |
| 2005/0043894 A1 | 2/2005 | Fernandez |
| 2005/0096584 A1 * | 5/2005 | Ferek-Petric .......... A61N 1/325 604/20 |
| 2005/0209642 A1 * | 9/2005 | Palti .................. A61N 1/326 607/2 |
| 2005/0222623 A1 | 10/2005 | Kroll et al. |
| 2005/0222646 A1 | 10/2005 | Kroll et al. |
| 2005/0288730 A1 | 12/2005 | Deem et al. |
| 2005/0288761 A1 | 12/2005 | Brabec et al. |
| 2006/0024802 A1 | 2/2006 | Muller et al. |
| 2006/0149341 A1 | 7/2006 | Palti |
| 2006/0190053 A1 | 8/2006 | Dobak |
| 2006/0259092 A1 | 11/2006 | Spadgenske et al. |
| 2006/0259099 A1 | 11/2006 | Goetz et al. |
| 2006/0282122 A1 | 12/2006 | Palti |
| 2006/0282126 A1 | 12/2006 | Fischbach et al. |
| 2007/0033660 A1 | 2/2007 | Palti |
| 2007/0135861 A1 | 6/2007 | Wallace et al. |
| 2007/0179550 A1 | 8/2007 | Dennis et al. |
| 2007/0225766 A1 | 9/2007 | Palti |
| 2007/0239213 A1 | 10/2007 | Palti |
| 2007/0239244 A1 | 10/2007 | Morgan et al. |
| 2007/0255340 A1 * | 11/2007 | Giftakis ............... A61N 1/0556 607/46 |
| 2007/0270675 A1 | 11/2007 | Kane et al. |
| 2007/0270916 A1 | 11/2007 | Fischell et al. |
| 2008/0058669 A1 | 3/2008 | Kroll |
| 2008/0058887 A1 * | 3/2008 | Griffin ............... A61N 1/36007 607/40 |

(56) References Cited

U.S. PATENT DOCUMENTS

| | | |
|---|---|---|
| 2008/0071350 A1 | 3/2008 | Stinson et al. |
| 2008/0086073 A1 | 4/2008 | McDaniel |
| 2008/0097424 A1 | 4/2008 | Wizeman et al. |
| 2008/0172116 A1* | 7/2008 | Mrva ................. A61N 1/0526 607/115 |
| 2008/0195227 A1 | 8/2008 | Boling et al. |
| 2008/0208271 A1 | 8/2008 | Sih et al. |
| 2008/0275524 A1 | 11/2008 | Furness et al. |
| 2009/0076500 A1 | 3/2009 | Azure et al. |
| 2009/0192381 A1 | 7/2009 | Brockway et al. |
| 2009/0234211 A1 | 9/2009 | Li et al. |
| 2010/0016936 A1 | 1/2010 | Stevenson et al. |
| 2010/0168820 A1 | 7/2010 | Maniak et al. |
| 2010/0191311 A1* | 7/2010 | Scheiner ............. A61B 5/4047 607/66 |
| 2010/0198298 A1* | 8/2010 | Glukhovsky ...... A61N 1/36021 607/46 |
| 2010/0217356 A1 | 8/2010 | Bikson et al. |
| 2010/0261994 A1 | 10/2010 | Davalos et al. |
| 2010/0298895 A1 | 11/2010 | Ghaffari et al. |
| 2010/0331938 A1* | 12/2010 | Sommer ............... A61N 1/056 607/116 |
| 2011/0071608 A1 | 3/2011 | Fleischhacker et al. |
| 2011/0077717 A1 | 3/2011 | Poletto |
| 2011/0125215 A1 | 5/2011 | Goetz et al. |
| 2011/0137229 A1 | 6/2011 | Palti et al. |
| 2011/0224665 A1 | 9/2011 | Crosby et al. |
| 2011/0238057 A1 | 9/2011 | Moss et al. |
| 2011/0306878 A1 | 12/2011 | Desimone et al. |
| 2012/0035616 A1* | 2/2012 | Olsen ..................... A61B 90/39 606/129 |
| 2012/0130444 A1 | 5/2012 | Wei et al. |
| 2012/0158072 A1* | 6/2012 | Venook ..................... A61N 1/05 607/116 |
| 2012/0158122 A1 | 6/2012 | Mattson et al. |
| 2012/0203307 A1 | 8/2012 | Schroeppel et al. |
| 2012/0232615 A1 | 9/2012 | Barolat et al. |
| 2012/0283726 A1 | 11/2012 | Palti |
| 2013/0023946 A1 | 1/2013 | Valvano et al. |
| 2013/0165916 A1 | 6/2013 | Mathur et al. |
| 2013/0204068 A1 | 8/2013 | Gnanashanmugam et al. |
| 2013/0261706 A1 | 10/2013 | Mirro et al. |
| 2013/0261711 A1 | 10/2013 | Sivo |
| 2013/0289649 A1 | 10/2013 | Averina et al. |
| 2013/0289664 A1 | 10/2013 | Johanek |
| 2013/0310898 A1* | 11/2013 | Ollivier ................ A61N 1/0534 607/62 |
| 2014/0005753 A1 | 1/2014 | Carbunaru |
| 2014/0052227 A1* | 2/2014 | Wahlstrand ............... A61N 1/05 607/116 |
| 2014/0094888 A1* | 4/2014 | True ..................... A61N 1/0556 607/118 |
| 2014/0107511 A1 | 4/2014 | Banet et al. |
| 2014/0142670 A1 | 5/2014 | Radhakrishnan et al. |
| 2014/0276781 A1 | 9/2014 | Beani et al. |
| 2014/0276811 A1 | 9/2014 | Koblish et al. |
| 2014/0350541 A1 | 11/2014 | Hill et al. |
| 2014/0350653 A1 | 11/2014 | Shiroff et al. |
| 2015/0005804 A1 | 1/2015 | Franano et al. |
| 2015/0066024 A1 | 3/2015 | Azure |
| 2015/0119952 A1 | 4/2015 | Sharma et al. |
| 2015/0134022 A1* | 5/2015 | Lee ..................... A61N 1/0534 607/9 |
| 2015/0180161 A1* | 6/2015 | Olson ................ H01R 13/5224 439/587 |
| 2015/0182282 A1 | 7/2015 | Zemel et al. |
| 2015/0320995 A1* | 11/2015 | Nazareth ............. A61N 1/0563 607/122 |
| 2015/0321000 A1* | 11/2015 | Rosenbluth .......... A61N 1/0456 607/48 |
| 2015/0353916 A1 | 12/2015 | Subramaniam et al. |
| 2015/0374992 A1 | 12/2015 | Crosby et al. |
| 2016/0022986 A1* | 1/2016 | Travers ................... A61N 1/32 607/59 |
| 2016/0029960 A1* | 2/2016 | Toth ................... A61B 18/1492 600/301 |
| 2016/0068598 A1 | 3/2016 | Yan et al. |
| 2016/0082258 A1 | 3/2016 | Kramer et al. |
| 2016/0121106 A1 | 5/2016 | Marshall et al. |
| 2016/0128767 A1 | 5/2016 | Azamian et al. |
| 2016/0129276 A1 | 5/2016 | Fried et al. |
| 2016/0175580 A1 | 6/2016 | Marshall et al. |
| 2016/0250476 A1 | 9/2016 | Kaemmerer et al. |
| 2016/0250483 A1* | 9/2016 | Klimovitch .......... A61N 1/3956 607/7 |
| 2016/0331459 A1 | 11/2016 | Townley et al. |
| 2016/0346536 A1 | 12/2016 | Palti et al. |
| 2017/0007310 A1 | 1/2017 | Rajagopalan et al. |
| 2017/0035496 A1 | 2/2017 | Nagale et al. |
| 2017/0049514 A1* | 2/2017 | Cosman ............... A61N 1/0551 |
| 2017/0065339 A1* | 3/2017 | Mickelsen ............. A61N 1/327 |
| 2017/0105793 A1 | 4/2017 | Cao et al. |
| 2017/0120041 A1 | 5/2017 | Wenger et al. |
| 2017/0173340 A1 | 6/2017 | Gupte et al. |
| 2017/0189098 A1 | 7/2017 | Azure et al. |
| 2017/0209691 A1* | 7/2017 | Sorajja ................. A61N 1/0502 |
| 2017/0215939 A1 | 8/2017 | Palti et al. |
| 2017/0231694 A1 | 8/2017 | Mathur et al. |
| 2017/0251976 A1 | 9/2017 | Schouenborg |
| 2017/0266371 A1 | 9/2017 | Leonhardt et al. |
| 2017/0281934 A1* | 10/2017 | Giladi ....................... A61N 1/32 |
| 2017/0281955 A1 | 10/2017 | Maile et al. |
| 2017/0312501 A1 | 11/2017 | Bornzin et al. |
| 2017/0333702 A1 | 11/2017 | Barner |
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0021563 A1 | 1/2018 | Van De Stolpe et al. |
| 2018/0050200 A1 | 2/2018 | Wasserman et al. |
| 2018/0110978 A1 | 4/2018 | Beebe et al. |
| 2018/0154142 A1 | 6/2018 | Guo et al. |
| 2018/0177431 A1 | 6/2018 | Rottenberg |
| 2018/0221088 A1 | 8/2018 | Govari et al. |
| 2018/0246079 A1 | 8/2018 | Wang et al. |
| 2018/0256906 A1 | 9/2018 | Pivonka et al. |
| 2018/0289954 A1* | 10/2018 | Hebb ................ A61N 1/36002 |
| 2019/0008555 A1 | 1/2019 | O'Mahony |
| 2019/0117962 A1 | 4/2019 | Chiang et al. |
| 2019/0117969 A1 | 4/2019 | Schmidt et al. |
| 2019/0117971 A1 | 4/2019 | Schmidt et al. |
| 2019/0117972 A1 | 4/2019 | Schmidt et al. |
| 2019/0117973 A1 | 4/2019 | Schmidt et al. |
| 2019/0255344 A1 | 8/2019 | Carter et al. |
| 2019/0262605 A1 | 8/2019 | Babakhani et al. |
| 2019/0321624 A1 | 10/2019 | De Kock et al. |
| 2019/0343398 A1 | 11/2019 | Zimmer |
| 2020/0009377 A1 | 1/2020 | Chang et al. |
| 2020/0061385 A1 | 2/2020 | Schwarz et al. |
| 2020/0197086 A1 | 6/2020 | Azamian et al. |
| 2020/0330756 A1 | 10/2020 | Schmidt et al. |
| 2020/0330757 A1 | 10/2020 | Schmidt et al. |
| 2020/0330758 A1 | 10/2020 | Schmidt et al. |
| 2020/0338344 A1 | 10/2020 | Schmidt et al. |
| 2020/0338345 A1 | 10/2020 | Schmidt et al. |
| 2020/0338346 A1 | 10/2020 | Schmidt et al. |
| 2021/0260370 A1 | 8/2021 | Srivastava et al. |
| 2021/0339015 A1 | 11/2021 | Dinsmoor et al. |
| 2022/0241586 A1 | 8/2022 | Spehr et al. |
| 2022/0288388 A1 | 9/2022 | Rondoni et al. |
| 2022/0296907 A1 | 9/2022 | Schmidt et al. |
| 2023/0218894 A1 | 7/2023 | Arnholt et al. |
| 2023/0330416 A1 | 10/2023 | Schmidt et al. |
| 2024/0024670 A1 | 1/2024 | Schmidt et al. |
| 2024/0115856 A1 | 4/2024 | Schmidt et al. |
| 2024/0226547 A1 | 7/2024 | Schmidt et al. |

FOREIGN PATENT DOCUMENTS

| | | |
|---|---|---|
| CN | 202365923 | 8/2012 |
| CN | 202844368 | 4/2013 |
| CN | 204698678 | 10/2015 |
| CN | 106823145 | 6/2017 |
| CN | 111278504 | 2/2025 |

(56) References Cited

FOREIGN PATENT DOCUMENTS

| | | | |
|---|---|---|---|
| CN | 113766948 | 2/2025 | |
| EP | 2942023 | 11/2015 | |
| EP | 4480526 | 12/2024 | |
| JP | 2011030734 | 2/2011 | |
| TW | 201039699 | 11/2010 | |
| WO | 9513113 | 5/1995 | |
| WO | 9526911 | 10/1995 | |
| WO | 9639966 | 12/1996 | |
| WO | 0158371 | 8/2001 | |
| WO | 0167098 | 9/2001 | |
| WO | 2006047833 | 5/2006 | |
| WO | 2008089360 | 7/2008 | |
| WO | 2009036457 | 3/2009 | |
| WO | 2013052590 | 4/2013 | |
| WO | 2014114433 | 7/2014 | |
| WO | 2015100451 | 7/2015 | |
| WO | 2016065263 | 4/2016 | |
| WO | 2016168485 | 10/2016 | |
| WO | 2016179712 | 11/2016 | |
| WO | WO-2016179712 A1 * | 11/2016 | ............. A61K 41/00 |
| WO | 2016199142 | 12/2016 | |
| WO | 2017123981 | 7/2017 | |
| WO | 2018207103 | 11/2018 | |
| WO | 2023137008 | 7/2023 | |

OTHER PUBLICATIONS

Di Sebastiano, Andrea R. et al., "Preclinical Outcomes of Intratumoral Modulation Therapy for Glioblastoma," Scientific Reports (2018) 8:7301 (11 pages).
Xu, Hu et al., "In Vitro Validation of Intratumoral Modulation Therapy for Glioblastoma," Anticancer Research 36:71-80 (2016), 10 pages.
International Search Report and Written Opinion for PCT Application No. PCT/US2018/057104 mailed Dec. 20, 2018 (14 pages).
International Search Report and Written Opinion for PCT Application No. PCT/US2018/057115 mailed Jan. 4, 2019 (13 pages).
International Search Report and Written Opinion for PCT Application No. PCT/US2018/057120 mailed Dec. 19, 2018 (14 pages).
International Search Report and Written Opinion for PCT Application No. PCT/US2018/057127 mailed Jan. 18, 2019 (12 pages).
International Preliminary Report on Patentability for PCT Application No. PCT/US2018/057104 mailed May 7, 2020 (8 pages).
International Preliminary Report on Patentability for PCT Application No. PCT/US2018/057115 mailed May 7, 2020 (9 pages).
International Preliminary Report on Patentability for PCT Application No. PCT/US2018/057117 mailed May 7, 2020 (8 pages).
International Preliminary Report on Patentability for PCT Application No. PCT/US2018/057120 mailed May 7, 2020 (8 pages).
International Preliminary Report on Patentability for PCT Application No. PCT/US2018/057127 mailed May 7, 2020 (8 pages).
Non-Final Office Action for U.S. Appl. No. 16/167,087 mailed May 27, 2020 (31 pages).
Response to Non-Final Rejection mailed on Apr. 6, 2020 for U.S. Appl. No. 16/167,140, submitted via EFS-Web on Jul. 6, 2020, 12 pages.
Response to Non-Final Rejection mailed on Mar. 20, 2020 for U.S. Appl. No. 16/166,957, submitted via EFS-Web on Jun. 3, 2020, 16 pages.
Non-Final Office Action for U.S. Appl. No. 16/167,140 mailed Apr. 6, 2020 (28 pages).
Non-Final Office Action for U.S. Appl. No. 16/166,957 mailed Mar. 20, 2020 (44 pages).
Final Office Action for U.S. Appl. No. 16/167,087 mailed Oct. 13, 2020 (21 pages).
Final Office Action for U.S. Appl. No. 16/167,140 mailed Oct. 19, 2020 (27 pages).
First Examination Report for Australian Patent Application No. 2018354162 mailed Sep. 29, 2020 (8 pages).
First Examination Report for Australian Patent Application No. 2018354167 mailed Sep. 14, 2020 (5 pages).
Non-Final Office Action for U.S. Appl. No. 16/167,116 mailed Oct. 7, 2020 (40 pages).
Response to Final Rejection mailed on Jul. 21, 2020 for U.S. Appl. No. 16/166,957, submitted via EFS-Web on Oct. 13, 2020, 16 pages.
Wang, Lijun et al., "Tumour Cell Membrane Poration and Ablation by Pulsed Low-Intensity Electric Field with Carbon Nanotubes," Int. J. Mol. Sci. 2015, 16, 6890-6901 (12 pages).
Final Office Action for U.S. Appl. No. 16/166,957 mailed Jul. 21, 2020 (30 pages).
First Examination Report for Australian Patent Application No. 2018354149 mailed Jul. 29, 2020 (5 pages).
First Examination Report for Australian Patent Application No. 2018354157 mailed Jul. 31, 2020 (5 pages).
First Examination Report for Australian Patent Application No. 2018354159 mailed Aug. 12, 2020 (5 pages).
Response to Non-Final Rejection mailed on May 27, 2020 for U.S. Appl. No. 16/167,087, submitted via EFS-Web on Aug. 20, 2020, 10 pages.
"Examination Report," for Australian Patent Application No. 2018354162 mailed Apr. 21, 2021 (5 pages).
"Final Office Action," for U.S. Appl. No. 16/166,957 mailed May 14, 2021 (33 pages).
"Office Action," for Japanese Patent Application No. 2020-542720 mailed May 11, 2021 (6 pages) No English Translation.
Communication Pursuant to Article 94(3) EPC for European Patent Application No. 18801137.3 mailed Mar. 5, 2021 (4 pages).
Examination Report for Australian Patent Application No. 2018354162 mailed Feb. 4, 2021 (5 pages).
Final Office Action for U.S. Appl. No. 16/167,116 mailed Jan. 21, 2021 (25 pages).
Giladi, Moshe et al., "Mitotic Spindle Disruption by Alternating Electric Fields Leads to Improper Chromosome Segregation and Mitotic Catastrophe in Cancer Cells," Sci Rep 5, 18046 (2016), 16 pages.
Non-Final Office Action for U.S. Appl. No. 16/166,957 mailed Feb. 17, 2021 (37 pages).
Non-Final Office Action for U.S. Appl. No. 16/167,087 mailed Mar. 31, 2021 (28 pages).
Office Action for Japanese Patent Application No. 2020-542718 mailed Feb. 9, 2021 11 pages) with English Translation.
Office Action for Japanese Patent Application No. 2020-542721 mailed Feb. 9, 2021 (10 pages) with English Translation.
Office Action for Japanese Patent Application No. 2020-542722 mailed Feb. 9, 2021 (5 pages) with English Summary.
Response to Examination Report for Australian Patent Application No. 2018354159 filed Jan. 18, 2021 (21 pages).
Response to Examination Report for Australian Patent Application No. 2018354162 filed Jan. 28, 2021 (15 pages).
Response to Examination Report for Australian Patent Application No. 2018354162 filed Mar. 30, 2021 (15 pages).
Response to Examination Report for Australian Patent Application No. 2018354167 filed Jan. 28, 2021 (17 pages).
Response to Final Rejection mailed on Jan. 21, 2021 for U.S. Appl. No. 16/167,116, submitted via EFS-Web on Mar. 2, 2021, 12 pages.
Response to Final Rejection mailed on Oct. 19, 2020 for U.S. Appl. No. 16/167,140, submitted via EFS-Web on Jan. 19, 2021, 16 pages.
Response to Non-Final Rejection mailed on Feb. 17, 2021 for U.S. Appl. No. 16/166,957, submitted via EFS-Web on Mar. 17, 2021, 17 pages.
Second Examination Report for Australian Patent Application No. 2018354149 mailed Jan. 8, 2021 (4 pages).
"Optune®—Elevate Expectations / Patient Information and Operation Manual," Novocure™, www.optune.com, 46, pages, Jan. 2019.
International Search Report and Written Opinion for PCT Application No. PCT/US2020/028508 mailed Aug. 3, 2020 (13 pages).
International Search Report and Written Opinion for PCT Application No. PCT/US2020/028509 mailed Jun. 30, 2020 (15 pages).
International Search Report and Written Opinion for PCT Application No. PCT/US2020/028512 mailed Jul. 13, 2020 (14 pages).
International Search Report and Written Opinion for PCT Application No. PCT/US2020/029270 mailed Oct. 26, 2020 (19 pages).

(56) References Cited

OTHER PUBLICATIONS

International Search Report and Written Opinion for PCT Application No. PCT/US2020/029274 mailed Aug. 28, 2020 (19 pages).
International Search Report and Written Opinion for PCT Application No. PCT/US2020/029277 mailed Jul. 13, 2020 (15 pages).
Invitation to Pay Additional Fees for PCT Application No. PCT/US2020/029270 mailed Aug. 28, 2020 (14 pages).
Invitation to Pay Additional Fees for PCT Application No. PCT/US2020/029274 mailed Jul. 7, 2020 (13 pages).
Kirson, Eilon D. et al., "Disruption of Cancer Cell Replication by Alternating Electric Fields," Cancer Research 64, 3288-3295, May 1, 2004 (8 pages).
"Novocure Announces Launch of the inovitro™," Laboratory Research System, Press Release, 2 pages, Nov. 21, 2013, 2 pages.
Response to Communication Pursuant to Rules 161(1) and 162 EPC for European Patent Application No. 18800411.3 filed Dec. 9, 2020 (11 pages).
Response to Communication Pursuant to Rules 161(1) and 162 EPC for European Patent Application No. 18801134.0 filed Dec. 11, 2020 (9 pages).
Response to Communication Pursuant to Rules 161(1) and 162 EPC for European Patent Application No. 18801136.5 filed Dec. 10, 2020 (8 pages).
Response to Communication Pursuant to Rules 161(1) and 162 EPC for European Patent Application No. 18801137.3 filed Dec. 10, 2020 (7 pages).
Response to Communication Pursuant to Rules 161(1) and 162 EPC for European Patent Application No. 18801138.1 filed Dec. 11, 2020 (16 pages).
Response to Examination Report for Australian Patent Application No. 2018354149 filed Dec. 21, 2020 (14 pages).
Response to Examination Report for Australian Patent Application No. 2018354157 filed Dec. 31, 2020 (17 pages).
Response to Final Rejection mailed Jul. 21, 2020 for U.S. Appl. No. 16/166,957, submitted via EFS-Web on Nov. 20, 2020, 21 pages.
Response to Final Rejection mailed on Oct. 13, 2020 for U.S. Appl. No. 16/167,087, submitted via EFS-Web on Jan. 13, 2021, 11 pages.
Response to Non-Final Rejection mailed on Oct. 7, 2020 for U.S. Appl. No. 16/167,116, submitted via EFS-Web on Jan. 6, 2021, 13 pages.
"Final Office Action," for U.S. Appl. No. 16/850,720 mailed Nov. 15, 2021 (15 pages).
"Final Office Action," for U.S. Appl. No. 16/855,421 mailed Nov. 5, 2021 (25 pages).
"International Preliminary Report on Patentability," for PCT Application No. PCT/US2020/028508 mailed Nov. 4, 2021 (8 pages).
"International Preliminary Report on Patentability," for PCT Application No. PCT/US2020/028509 mailed Nov. 4, 2021 (9 pages).
"International Preliminary Report on Patentability," for PCT Application No. PCT/US2020/028512 mailed Nov. 4, 2021 (8 pages).
"International Preliminary Report on Patentability," for PCT Application No. PCT/US2020/029270 mailed Nov. 4, 2021 (11 pages).
"International Preliminary Report on Patentability," for PCT Application No. PCT/US2020/029274 mailed Nov. 4, 2021 (13 pages).
"International Preliminary Report on Patentability," for PCT Application No. PCT/US2020/029277 mailed Nov. 4, 2021 (10 pages).
"Office Action," for Canadian Patent Application No. 3,079,316 mailed Oct. 27, 2021 (4 pages).
"Response to Examination Report," for Canadian Patent Application No. 3,079,213 filed Nov. 10, 2021 (13 pages).
"Response to Examination Report," for Canadian Patent Application No. 3,079,282 filed Nov. 10, 2021 (13 pages).
"Response to Final Rejection mailed on," Aug. 2, 2021 for U.S. Appl. No. 16/167,087, submitted via EFS-Web on Nov. 1, 2021, 12 pages.
"Response to Non-Final Rejection," mailed on Aug. 24, 2021 for U.S. Appl. No. 16/850,720, submitted via EFS-Web on Nov. 1, 2021, 11 pages.
"Response to Non-Final Rejection," mailed on Sep. 3, 2021 for U.S. Appl. No. 16/167,116, submitted via EFS-Web on Nov. 2, 2021, 14 pages.
"Response to Non-Final Rejection," mailed on Sep. 8, 2021 for U.S. Appl. No. 16/855,433, submitted via EFS-Web on Nov. 2, 2021, 12 pages.
"Response to Office Action," for Canadian Patent Application No. 3,079,314 filed Nov. 12, 2021 (14 pages).
"Decision of Rejection," for Japanese Patent Application No. 2020-54219 mailed Oct. 19, 2021 (6 pages) with English Translation.
"Final Office Action," for U.S. Appl. No. 16/167,140 mailed Dec. 27, 2021 (30 pages).
"Non-Final Office Action," for U.S. Appl. No. 16/166,957 mailed Dec. 22, 2021 (39 pages).
"Non-Final Office Action," for U.S. Appl. No. 16/167,087 mailed Dec. 22, 2021 (24 pages).
"Response to Final Rejection," mailed on Nov. 5, 2021 for U.S. Appl. No. 16/855,421, submitted via EFS-Web on Jan. 5, 2022, 11 pages.
"Response to Office Action," for Canadian Patent Application No. 3,079,316 filed Dec. 31, 2021 (15 pages).
"Communication Pursuant to Article 94(3) EPC," for European Patent Application No. 18801137.3 mailed Sep. 15, 2021 (4 pages).
"Communication Pursuant to Article 94(3) EPC," for European Patent Application No. 18801138.1 mailed Jun. 7, 2021 (7 pages).
"Examination Report," for Canadian Patent Application No. 3,079,213 mailed Jul. 12, 2021 (4 pages).
"Examination Report," for Canadian Patent Application No. 3,079,282 mailed Jul. 14, 2021 (4 pages).
"Examination Report," for Canadian Patent Application No. 3,079,314 mailed Jul. 14, 2021 (4 pages).
"Final Office Action," for U.S. Appl. No. 16/167,087 mailed Aug. 2, 2021 (25 pages).
"First Office Action," for Chinese Patent Application No. 201880068896.3 mailed Apr. 13, 2021 (17 pages) with English Summary.
"First Office Action," for Chinese Patent Application No. 201880078117.8 mailed Jul. 20, 2021 (14 pages) with English Summary.
"International Search Report and Written Opinion," for PCT Application No. PCT/US2021/019160 mailed Jun. 2, 2021 (15 pages).
"Non-Final Office Action," for U.S. Appl. No. 16/167,116 mailed Sep. 3, 2021 (29 pages).
"Non-Final Office Action," for U.S. Appl. No. 16/167,140 mailed Jul. 12, 2021 (32 pages).
"Non-Final Office Action," for U.S. Appl. No. 16/850,720 mailed Aug. 24, 2021 (32 pages).
"Non-Final Office Action," for U.S. Appl. No. 16/855,421 mailed May 28, 2021 (37 pages).
"Non-Final Office Action," for U.S. Appl. No. 16/855,433 mailed Sep. 8, 2021 (32 pages).
"Office Action," for Canadian Patent Application No. 3,079,289 mailed May 28, 2021 (4 pages).
"Office Action," for Japanese Patent Application No. 2020-542719 mailed Jun. 1, 2021 (9 pages) with English Translation.
"Response to Communication Pursuant to Article 94(3) EPC," for European Patent Application No. 18801138.1 filed Oct. 15, 2021 (10 pages).
"Response to Examination Report," for Australian Patent Application No. 2018354162 filed Jul. 13, 2021 (18 pages).
"Response to Final Rejection," mailed on May 14, 2021 and Advisory Action mailed on Aug. 26, 2021 for U.S. Appl. No. 16/166,957, submitted via EFS-Web on Sep. 10, 2021.
"Response to Final Rejection," mailed on May 14, 2021 for U.S. Appl. No. 16/166,957, submitted via EFS-Web on Aug. 5, 2021, 18 pages.
"Response to Non-Final Rejection," mailed on Jul. 12, 2021 for U.S. Appl. No. 16/167,140, submitted via EFS-Web on Oct. 12, 2021, 16 pages.
"Response to Non-Final Rejection," mailed on Mar. 31, 2021 for U.S. Appl. No. 16/167,087, submitted via EFS-Web on Jun. 23, 2021, 12 pages.

(56) References Cited

OTHER PUBLICATIONS

"Response to Non-Final Rejection," mailed on May 28, 2021 for U.S. Appl. No. 16/855,421, submitted via EFS-Web on Aug. 20, 2021, 11 pages.
"Response to Office Action," for Canadian Patent Application No. 3,079,289 filed with CIPO Sep. 23, 2021 (17 pages).
"Response to Second Examination Report," for Australian Patent Application No. 2018354149 filed Apr. 13, 2021 (19 pages).
"Final Office Action," for U.S. Appl. No. 16/855,433 mailed Feb. 1, 2022 (20 pages).
"Non-Final Office Action," for U.S. Appl. No. 16/850,712 mailed Jan. 21, 2022 (40 pages).
"Non-Final Office Action," for U.S. Appl. No. 17/182,436 mailed Feb. 1, 2022 (41 pages).
"Notice of Allowance," for U.S. Appl. No. 16/167,116 mailed Jan. 26, 2022 (19 pages).
"Office Action," for Japanese Patent Application No. 2020-542721 mailed Jan. 4, 2022 (3 pages) with English summary.
"Response to Communication Pursuant to Art. 94(3) EPC," for European Patent Application No. 18801137.3 filed Jan. 13, 2022 (8 pages).
"Response to Final Rejection," mailed on Dec. 27, 2021 for U.S. Appl. No. 16/167,140, submitted via EFS-Web on Feb. 9, 2022, 9 pages.
"Response to Final Rejection," mailed on Nov. 15, 2021 for U.S. Appl. No. 16/850,720, submitted via EFS-Web on Feb. 11, 2022, 12 pages.
"Response to Final Rejection," mailed on Nov. 5, 2021 and Advisory Action mailed on Feb. 9, 2022 for U.S. Appl. No. 16/855,421, submitted via EFS-Web on Mar. 4, 2022.
"Notice of Allowance," for U.S. Appl. No. 16/850,720 mailed Apr. 14, 2022 (17 pages).
"Office Action," for Canadian Patent Application No. 3,079,213 mailed Apr. 20, 2022 (6 pages).
"Office Action," for Canadian Patent Application No. 3,079,289 mailed Mar. 24, 2022 (8 pages).
"Office Action," for Japanese Patent Application No. 2020-542722 mailed Oct. 26, 2021 (9 pages) with English Translation.
"Response to Final Rejection," mailed on Dec. 27, 2021 and Advisory Action mailed on Mar. 9, 2022 for U.S. Appl. No. 16/167,140, submitted via EFS-Web on Mar. 25, 2022, 11 pages.
"Response to Final Rejection," mailed on Feb. 1, 2022 for U.S. Appl. No. 16/855,433, submitted via EFS-Web on May 2, 2022, 9 pages.
"Response to Non-Final Rejection," mailed on Dec. 22, 2021 for U.S. Appl. No. 16/166,957, submitted via EFS-Web on Mar. 22, 2022, 13 pages.
"Response to Non-Final Rejection," mailed on Dec. 22, 2021 for U.S. Appl. No. 16/167,087, submitted via EFS-Web on Mar. 22, 2022, 9 pages.
"Response to Non-Final Rejection," mailed on Feb. 1, 2022 for U.S. Appl. No. 17/182,436, submitted via EFS-Web on Mar. 21, 2022, 8 pages.
"Response to Non-Final Rejection," mailed on Jan. 21, 2022 for U.S. Appl. No. 16/850,712, submitted via EFS-Web on Mar. 21, 2022, 10 pages.
"Second Office Action," for Chinese Patent Application No. 201880068896.3 Oct. 20, 2021 (14 pages), with English summary.
"First Office Action," for Chinese Patent Application No. 201880068897.8 mailed Sep. 21, 2022 (11 pages) with English Summary.
"Non-Final Office Action," for U.S. Appl. No. 16/855,448 mailed Nov. 7, 2022 (58 pages).
"Non-Final Office Action," for U.S. Appl. No. 16/166,957 mailed Sep. 29, 2022 (41 pages).
"Response to Final Rejection," mailed on Jul. 22, 2022 with Request for Continued Examination, for U.S. Appl. No. 17/182,436, submitted via EFS-Web on Sep. 29, 2022, 9 pages.
"Response to Final Rejection," mailed on Jul. 27, 2022 for U.S. Appl. No. 17/182,436, submitted via EFS-Web on Sep. 27, 2022, 9 pages.
"Response to Final Rejection," mailed on Jul. 5, 2022 and Advisory Action mailed on Sep. 15, 2022 for U.S. Appl. No. 16/850,712, submitted via EFS-Web on Sep. 23, 2022, 10 pages.
"Non-Final Office Action," for U.S. Appl. No. 16/850,712 mailed Oct. 6, 2022 (11 pages).
"Final Office Action," for U.S. Appl. No. 16/166,957 mailed May 18, 2022 (35 pages).
"Final Office Action," for U.S. Appl. No. 16/167,087 mailed May 18, 2022 (26 pages).
"Final Office Action," for U.S. Appl. No. 16/850,712 mailed Jul. 5, 2022 (16 pages).
"Final Office Action," for U.S. Appl. No. 17/182,436 mailed Jul. 27, 2022 (19 pages).
"International Search Report and Written Opinion," for PCT Application No. PCT/US2022/021161 mailed Jun. 22, 2022 (15 pages).
"Non-Final Office Action," for U.S. Appl. No. 16/167,140 May 27, 2022 (25 pages).
"Non-Final Office Action," for U.S. Appl. No. 16/855,421 mailed Jun. 7, 2022 (21 pages).
"Non-Final Office Action," for U.S. Appl. No. 16/855,433 mailed May 27, 2022 (18 pages).
"Office Action Response," for Canadian Patent Application No. 3,079,289 filed Jul. 18, 2022 (17 pages).
"Office Action Response," for Canadian Patent Application No. 3,079,314 filed Aug. 11, 2022 (7 pages).
"Office Action," for Canadian Patent Application No. 3,079,314 mailed Apr. 29, 2022 (3 pages).
"Office Action," for Canadian Patent Application No. 3,079,316 mailed Jun. 3, 2022 (3 pages).
"Response to Communication Pursuant to Rules 161(1) and 162 EPC," for European Patent Application No. 20724332.0 filed May 11, 2022 (24 pages).
"Response to Communication Pursuant to Rules 161(1) and 162 EPC," for European Patent Application No. 20724702.4 filed May 11, 2022 (24 pages).
"Response to Communication Pursuant to Rules 161(1) and 162 EPC," for European Patent Application No. 20724703.2 filed Jun. 8, 2022 (12 pages).
"Response to Communication Pursuant to Rules 161(1) and 162 EPC," for European Patent Application No. 20727417.6 filed Jun. 1, 2022 (8 pages).
"Response to Communication Pursuant to Rules 161(1) and 162 EPC," for European Patent Application No. 20724333.8 filed Jun. 8, 2022 (8 pages).
"Response to Final Rejection," mailed on May 18, 2022 for U.S. Appl. No. 16/166,957, submitted via EFS-Web on Aug. 18, 2022, 14 pages.
"Response to Final Rejection," mailed on May 18, 2022 for U.S. Appl. No. 16/167,087, submitted via EFS-Web on Aug. 18, 2022, 9 pages.
"Response to Non-Final Rejection," mailed on May 27, 2022 for U.S. Appl. No. 16/167,140, submitted via EFS-Web on Aug. 25, 2022, 14 pages.
"Response to Non-Final Rejection," mailed on May 27, 2022 for U.S. Appl. No. 16/855,433, submitted via EFS-Web on Aug. 25, 2022, 9 pages.
"Response to Office Action," for Canadian Patent Application No. 3,079,213 filed Aug. 10, 2022 (10 pages).
"Third Office Action," for Japanese Patent Application No. 2020-542721 mailed Aug. 23, 2022 (5 pages) No English Translation.
Notice of Opposition for European Patent Application No. 18801134.0 on behalf of Novocure Gmbh, mailed Jun. 28, 2022 (36 pages).
"Communication Pursuant to Article 94(3) EPC," for European Patent Application No. 18800411.3 mailed Dec. 22, 2022 (5 pages).
"Non-Final Office Action," for U.S. Appl. No. 16/167,140 Nov. 15, 2022 (29 pages).
"Non-Final Office Action," for U.S. Appl. No. 16/850,728 mailed Jan. 24, 2023 (68 pages).
"Non-Final Office Action," for U.S. Appl. No. 16/855,433 mailed Nov. 17, 2022 (39 pages).

(56) References Cited

OTHER PUBLICATIONS

"Non-Final Office Action," for U.S. Appl. No. 17/182,436 mailed Nov. 23, 2022 (19 pages).
"Notice of Allowance," For U.S. Appl. No. 16/850,712 Mailed Feb. 7, 2023 (14 pages).
"Notice of Allowance," for U.S. Appl. No. 16/855,421 mailed Nov. 16, 2022 (17 pages).
"Office Action," for Canadian Patent Application No. 3,079,213 mailed Dec. 5, 2022 (4 pages).
"Office Action," for Canadian Patent Application No. 3,079,289 mailed Nov. 28, 2022 (7 pages).
"Office Action," for Japanese Patent Application No. 2021-562795 mailed Nov. 15, 2022 (5 pages) with English Translation.
"Office Action," for Japanese Patent Application No. 2021-562797 mailed Nov. 22, 2022 (9 pages), with English Translation.
"Office Action," for Japanese Patent Application No. 2021-562798 mailed Nov. 15, 2022 (14 pages), with English translation.
"Office Action," for Japanese Patent Application No. 2021-562966 mailed Nov. 29, 2022 (11 pages) with English Translation.
"Office Action," for Japanese Patent Application No. 2021-562972 mailed Nov. 8, 2022 (26 pages) with English Translation.
"Response to Communication Pursuant to Rules 161(1) and 162 EPC," for European Patent Application No. 21712639.0 filed Jan. 20, 2023 (26 pages).
"Response to Non-Final Rejection," mailed on Nov. 7, 2022 for U.S. Appl. No. 16/855,448, submitted via EFS-Web on Feb. 7, 2023, 9 pages.
"Response to Non-Final Rejection," mailed on Oct. 6, 2022 for U.S. Appl. No. 16/850,712, submitted via EFS-Web on Jan. 4, 2023, 10 pages.
"Response to Non-Final Rejection," mailed on Sep. 15, 2022 for U.S. Appl. No. 16/167,087, submitted via EFS-Web on Dec. 13, 2022, 8 pages.
"Response to Non-Final Rejection," mailed on Sep. 29, 2022 for U.S. Appl. No. 16/166,957, submitted via EFS-Web on Dec. 13, 2022, 16 pages.
"Communication Pursuant to Article 94(3) EPC," for European Patent Application No. 18801138.1 mailed Aug. 29, 2022 (5 pages).
"International Preliminary Report on Patentability," for PCT Application No. PCT/US2021/019160 mailed Sep. 9, 2022 (10 pages).
"Non-Final Office Action," for U.S. Appl. No. 16/167,087 mailed Sep. 15, 2022 (24 pages).
"Notice of Opposition," for European Patent No. 3700627 filed Aug. 24, 2022 (20 pages).
"Response to Final Rejection," mailed on Jul. 5, 2022 for U.S. Appl. No. 16/850,712, submitted via EFS-Web on Sep. 6, 2022, 10 pages.
"Response to Non-Final Rejection," mailed on Jun. 7, 2022 for U.S. Appl. No. 16/855,421, submitted via EFS-Web on Sep. 7, 2022, 9 pages.
"Communication Pursuant to Article 94(3) EPC," for European Patent Application No. 18801138.1 mailed Jul. 7, 2023 (5 pages).
"Decision of Rejection," for Japanese Patent Application No. 2021-562797 mailed May 16, 2023 (10 pages), with English translation.
"Final Office Action," for U.S. Appl. No. 16/850,728 mailed Jun. 26, 2023 (26 pages).
"Office Action," for Canadian Patent Application No. 3,079,289 mailed Jul. 6, 2023 (3 pages).
"Office Action," for Japanese Patent Application No. 2021-562972 mailed May 5, 2023 (12 pages), with English translation.
"Response to Communication Pursuant to Article 94(3) EPC," for European Patent Application No. 20724333.8 filed Jul. 25, 2023 (28 pages).
"Response to Final Rejection," mailed on May 3, 2023, for U.S. Appl. No. 16/855,433, submitted via EFS-Web on Aug. 2, 2023, 10 pages.
"Second Office Action," for Japanese Patent Application No. 2021-562966 mailed Jun. 13, 2023 (9 pages), with English translation.
"Third Office Action," for Chinese Patent Application No. 201880068897.8 mailed Jun. 9, 2023 (10 pages) with English Summary.
"Communication Pursuant to Article 94(3) EPC," for European Patent Application No. 20724333.8 mailed Mar. 17, 2023 (6 pages).
"Decision of Rejection," for Japanese Patent Application No. 2021-562795 mailed Mar. 28, 2023 (6 pages) with English translation.
"Final Office Action," for Japanese Patent Application No. 2020-542721 mailed Mar. 7, 2023 (5 pages) with English translation.
"Final Office Action," for U.S. Appl. No. 16/166,957 mailed Mar. 7, 2023 (49 pages).
"Final Office Action," for U.S. Appl. No. 16/167,087 mailed Mar. 6, 2023 (30 pages).
"Final Office Action," for U.S. Appl. No. 16/167,140 mailed May 24, 2023 (41 pages).
"Final Office Action," for U.S. Appl. No. 16/855,433 mailed May 3, 2023 (25 pages).
"Final Office Action," for U.S. Appl. No. 17/182,436 mailed May 19, 2023 (22 pages).
"First Office Action," for Chinese Patent Application No. 201880068852.0 mailed Mar. 15, 2023 (9 pages).
"First Office Action," for Chinese Patent Application No. 201880078118.2 mailed Mar. 27, 2023 (17 pages) with English translation.
"International Search Report and Written Opinion," for PCT Application No. PCT/US2023/010469 mailed Apr. 12, 2023 (19 pages).
"Notice of Allowance," for U.S. Appl. No. 16/855,448 mailed Mar. 8, 2023 (19 pages).
"Response to Communication Pursuant to Article 94(3) EPC," for European Patent Application No. 18800411.3 filed May 2, 2023 (11 pages).
"Response to Communication Pursuant to Article 94(3) EPC," for European Patent Application No. 18801138.1 filed Mar. 8, 2023 (10 pages).
"Response to Final Rejection," mailed Mar. 6, 2023 for U.S. Appl. No. 16/167,087, submitted via EFS-Web on Jun. 6, 2023, 10 pages.
"Response to Final Rejection," mailed on Mar. 7, 2023 for U.S. Appl. No. 16/166,957, submitted via EFS-Web on Jun. 7, 2023, 18 pages.
"Response to Non-Final Rejection," for U.S. Appl. No. 16/855,433, mailed on Nov. 17, 2022, submitted via EFS-Web on Feb. 17, 2023, 11 pages.
"Response to Non-Final Rejection," mailed on Jan. 24, 2023 for U.S. Appl. No. 16/850,728, submitted via EFS-Web on Apr. 20, 2023, 8 pages.
"Response to Non-Final Rejection," mailed on Nov. 15, 2022, based on U.S. Appl. No. 16/167,140, submitted via EFS-Web on Feb. 15, 2023, 12 pages.
"Response to Non-Final Rejection," mailed on Nov. 23, 2022 for U.S. Appl. No. 17/182,436, submitted via EFS-Web on Feb. 23, 2023, 11 pages.
"Response to Office Action," for Canadian Patent Application No. 3,079,213 filed Mar. 8, 2023 (6 pages).
"Response to Office Action," for Canadian Patent Application No. 3,079,289 filed Mar. 24, 2023 (18 pages).
"Second Office Action," for Chinese Patent Application No. 201880068897.8 mailed Feb. 27, 2023 (9 pages) with English Summary.
"Second Office Action," for Japanese Patent Application No. 2021-562798 mailed May 9, 2023 (11 pages) with English translation.
"Decision of Rejection," for Japanese Patent Application No. 2021-562972 mailed Sep. 5, 2023 (10 pages) with English Translation.
"First Office Action," for Chinese Patent Application No. 202080030771.9 mailed Nov. 15, 2023 (7 pages) with English summary.
"Fourth Office Action," for Chinese Patent Application No. 201880068897.8 mailed Oct. 17, 2023 (13 pages) with English Summary.
"International Preliminary Report on Patentability," for PCT Application No. PCT/US2022/021161 mailed Oct. 5, 2023 (9 pages).
"Non-Final Office Action," for U.S. Appl. No. 16/166,957 mailed Nov. 14, 2023 (39 pages).
"Non-Final Office Action," for U.S. Appl. No. 16/167,087 mailed Sep. 19, 2023 (38 pages).
"Non-Final Office Action," for U.S. Appl. No. 16/167,140 mailed Oct. 11, 2023 (32 pages).

(56) References Cited

OTHER PUBLICATIONS

"Notice of Allowance," for U.S. Appl. No. 16/855,433 mailed Aug. 23, 2023 (6 pages).
"Notice of Allowance," for U.S. Appl. No. 17/182,436 mailed Sep. 15, 2023 (17 pages).
"Office Action," for Japanese Patent Application No. 2021-562798 mailed Aug. 22, 2023 (4 pages) with English translation.
"Response to Communication Pursuant to Article 94(3) EPC," for European Patent Application No. 18801138.1 filed Nov. 16, 2023 (76 pages).
"Response to Final Office Action," mailed May 24, 2023, and Advisory Action mailed Sep. 20, 2023, for U.S. Appl. No. 16/167,140, submitted via EFS-Web on Sep. 25, 2023, 12 pages.
"Response to Final Rejection," mailed on Jun. 26, 2023 for U.S. Appl. No. 16/850,728, submitted via EFS-Web on Sep. 26, 2023, 11 pages.
"Response to Final Rejection," mailed on May 19, 2023, for U.S. Appl. No. 17/182,436, submitted via EFS-Web on Aug. 21, 2023, 14 pages.
"Response to Final Rejection," mailed on May 24, 2023, for U.S. Appl. No. 16/167,140, submitted via EFS-Web on Aug. 24, 2023, 11 pages.
"Response to Non-Final Rejection," mailed on Sep. 19, 2023, for U.S. Appl. No. 16/167,087, submitted via EFS-Web on Dec. 19, 2023, 13 pages.
"Response to Office Action," for Canadian Patent Application No. 3,079,289 filed Nov. 3, 2023 (13 pages).
"Summons to Attend Oral Proceedings," for European Patent Application No. 18801136.5 mailed Sep. 12, 2023 (13 pages).
"Supplemental Response to," Final Rejection mailed on Mar. 6, 2023, for U.S. Appl. No. 16/167,087, submitted via EFS-Web on Aug. 31, 2023, 7 pages.
"Written Submissions," as filed in response to Summons to Attend Oral Proceedings for European Patent Application No. 18801134.0 filed Dec. 20, 2023 (137 pages).
"Zenchi Examination Report," for Japanese Patent Application No. 2021-562795 mailed Aug. 2, 2023 (9 pages) with English Summary.
"Communication Pursuant to Article 94(3) EPC," for European Patent Application No. 20724703.2 mailed Jun. 4, 2024 (7 pages).
"Decision of Rejection," for Japanese Patent Application No. 2021-562966 mailed Dec. 26, 2023 (9 pages), with English translation.
"Extended European Search Report," for European Patent Application No. 24159633.7 mailed Jun. 14, 2024 (7 pages).
"Extended European Search Report," for European Patent Application No. 24171838.6 mailed May 8, 2024 (6 pages).
"Extended European Search Report," for European Patent Application No. 24171875.8 mailed Jul. 16, 2024 (8 pages).
"Fifth Office Action," for Chinese Patent Application No. 201880068897.8 mailed Feb. 8, 2024 (8 pages) with English summary.
"Final Office Action," for U.S. Appl. No. 16/166,957 mailed May 31, 2024 (49 pages).
"Final Office Action," for U.S. Appl. No. 16/167,087 mailed Apr. 1, 2024 (38 pages).
"Final Office Action," for U.S. Appl. No. 16/167,140 mailed Feb. 7, 2024 (42 pages).
"Final Rejection Action," for Chinese Patent Application No. 201880078118.2 mailed Mar. 28, 2024 (10 pages) with English translation, 12 pages.
"First Office Action," for Chinese Patent Application No. 202080030415.7 mailed Mar. 6, 2024 (13 pages) with English translation.
"First Office Action," for Chinese Patent Application No. 202080030769.1 mailed Dec. 29, 2023, with English summary (12 pages).
"First Office Action," for Chinese Patent Application No. 202080030850.X mailed Mar. 29, 2024 (14 pages) with English translation.
"First Office Action," for Chinese Patent Application No. 202080030856.7 mailed Mar. 16, 2024 (11 pages) with English translation.
"Non-Final Office Action," for U.S. Appl. No. 16/850,728 mailed Feb. 14, 2024 (33 pages).
"Non-Final Office Action," for U.S. Appl. No. 17/698,516 mailed Feb. 23, 2024 (69 pages).
"Non-Final Office Action," for U.S. Appl. No. 18/123,776 mailed Mar. 20, 2024 (40 pages).
"Non-Final Office Action," for U.S. Appl. No. 18/215,603 mailed Jul. 18, 2024, 64 pages.
"Non-Final Office Action," for U.S. Appl. No. 18/227,021 mailed May 31, 2024 (61 pages).
"Notice of Allowance," for U.S. Appl. No. 16/850,728 mailed Jun. 5, 2024 (17 pages).
"Office Action," for Japanese Patent Application No. 2021-562795 mailed Jun. 18, 2024 (8 pages) with English translation.
"Response to Final Rejection," mailed Feb. 7, 2024, and the Advisory Action mailed on Jun. 4, 2024, for U.S. Appl. No. 16/167,140, submitted via EFS-Web on Jul. 2, 2024, 14 pages.
"Response to Final Rejection," mailed on Feb. 7, 2024, for U.S. Appl. No. 16/167,140, submitted via EFS-Web on May 7, 2024, 12 pages.
"Response to Non-Final Rejection," mailed on Feb. 14, 2024, for U.S. Appl. No. 16/850,728, submitted via EFS-Web on May 14, 2024, 12 pages.
"Response to Non-Final Rejection," mailed on Feb. 23, 2024, for U.S. Appl. No. 17/698,516, submitted via EFS-Web on May 20, 2024, 9 pages.
"Response to Non-Final Rejection," mailed on Mar. 20, 2024, for U.S. Appl. No. 18/123,776, submitted via EFS-Web on Jun. 20, 2024, 8 pages.
"Response to Non-Final Rejection," mailed on Nov. 14, 2024, for U.S. Appl. No. 16/166,957, submitted via EFS-Web on Feb. 14, 2024, 15 pages.
"Response to Non-Final Rejection," mailed on Oct. 11, 2024, for U.S. Appl. No. 16/167,140, submitted via EFS-Web on Jan. 11, 2024, 12 pages.
"Second Office Action," for Chinese Patent Application No. 201880068852.0 mailed Jan. 15, 2024 (19 pages) with English summary.
"Second Office Action," for Chinese Patent Application No. 201880078118.2 mailed Jan. 12, 2024 (17 pages) with English translation.
Chen, Yu, et al."Synergistic chemo-photodynamic therapy mediated by light-activated ROS-degradable nanocarriers.," Synergistic chemo-photodynamic therapy mediated by light-activated ROS-degradable nanocarriers. J. Mater. Chem. B, 2019, 7, 460-468. Apr. 12, 2018 (Chen et al) https://pubs.rsc.org/en/content/articlelanding/20 1 9/tb/c8tb03030h, 460-468.
"Extended European Search Report," for European Patent Application No. 24191767.3 mailed Nov. 13, 2024 (10 pages).
"Final Office Action," for U.S. Appl. No. 17/698,516 mailed Aug. 19, 2024 (25 pages).
"Final Office Action," for U.S. Appl. No. 18/227,021 mailed Sep. 18, 2024 (15 pages).
"Final Rejection Action," for Chinese Patent Application No. 201880068852.0 mailed Jun. 7, 2024 (16 pages) with English Summary.
"International Preliminary Report on Patentability," for PCT Patent Application No. PCT/US2023/010469 mailed Jul. 25, 2024 (12 pages).
"Non-Final Rejection," mailed on Nov. 7, 2024, for U.S. Appl. No. 16/167,140, 50 pages.
"Notice of Allowance," for U.S. Appl. No. 18/123,776 mailed Sep. 9, 2024 (13 pages).
"Response to Communication Pursuant to Article 94(3) EPC," for European Patent Application No. 20724703.2 filed Sep. 25, 2024 (27 pages).
"Response to Final Rejection," mailed Aug. 19, 2024, for U.S. Appl. No. 17/968,516, submitted via Patent Center on Dec. 4, 2024, 12 pages.

(56) References Cited

OTHER PUBLICATIONS

"Response to Final Rejection," mailed on Aug. 19, 2024, for U.S. Appl. No. 17/698,516, submitted via Patent Center on Nov. 12, 2024, 12 pages.

"Response to Final Rejection," mailed on Jun. 18, 2024, for U.S. Appl. No. 16/167,087, submitted via Patent Center on Sep. 17, 2024, 12. pages.

"Response to Final Rejection," mailed on May 31, 2024, and the Advisory Action mailed on Sep. 19, 2024, for U.S. Appl. No. 16/166,957 submitted via Patent Center on Sep. 27, 2024, 18 pages.

"Response to Final Rejection," mailed on May 31, 2024, for U.S. Appl. No. 16/166,957, submitted via EFS-Web on Aug. 30, 2024, 18 pages.

"Response to Non-Final Rejection," mailed on Jul. 18, 2024, for U.S. Appl. No. 18/215,603, submitted via Patent Center on Oct. 17, 2024, 8 pages.

"Response to Non-Final Rejection," mailed on May 31, 2024, for U.S. Appl. No. 18/227,021, submitted via Patent Center on Sep. 3, 2024, 8 pages.

"Second Office Action," for Chinese Patent Application No. 202080030769.1 mailed Jul. 4, 2024 (13 pages) with English translation.

"Second Office Action," for Chinese Patent Application No. 202080030850.X mailed Nov. 12, 2024 (8 pages) with English translation.

"Second Office Action," for Chinese Patent Application No. 202080030856.7 mailed Nov. 9, 2024 (9 pages) with English Summary.

"Supplemental Amendment," filed in response to Non-Final Rejection mailed Mar. 20, 2024, for U.S. Appl. No. 18/123,776, submitted via Patent center on Aug. 30, 2024, 12 pages.

"Zenchi Examination Report," for Japanese Patent Application No. 2021-562966 mailed Aug. 6, 2024 (3 pages) with English Translation.

Santhosh, Sheeba, et al. "Impact of Electrodes Separation Distance on Bio-impedance Diagnosis.," Biomedical & Pharmacology Journal, Mar. 2021. 14(1), p. 141-146. (Year: 2021).

"Extended European Search Report," for European Patent Application No. 24205287.6 mailed Feb. 7, 2025 (9 pages).

"Final Rejection," for Chinese Patent Application No. 202080030856.7 mailed Jan. 21, 2025, 7 pages.

"Non-Final Office Action," for U.S. Appl. No. 16/166,957 mailed Dec. 23, 2024 (49 pages).

"Non-Final Office Action," for U.S. Appl. No. 16/167,087 mailed Feb. 18, 2025 (50 pages).

"Non-Final Office Action," for U.S. Appl. No. 16/167,140 mailed Mar. 10, 2025 (42 pages).

"Non-Final Office Action," for U.S. Appl. No. 18/227,021 mailed Mar. 6, 2025 (15 pages).

"Notice of Allowance," for U.S. Appl. No. 18/215,603 mailed Jan. 23, 2025 (11 pages).

"Response to Extended European Search Report," for European Patent Application No. 24171875.8 filed Feb. 17, 2025 (24 pages).

"Response to Final Rejection mailed on," Sep. 18, 2024, for U.S. Appl. No. 18/227,021 submitted via Patent Center on Dec. 18, 2024, 10 pages.

"Response to Non-Final Rejection," mailed on Dec. 23, 2024, for U.S. Appl. No. 16/166,957, submitted via EFS-Web on Mar. 24, 2025, 20 pages.

"Response to Non-Final Rejection," mailed on Nov. 7, 2024, for U.S. Appl. No. 16/167,140, submitted via EFS-Web on Feb. 7, 2025, 11 pages.

Schneiderman, et al., "Overcoming cell size escape from tumor treating fields using a varying frequency treatment paradigm in vitro," Meeting Abstract: 2013 ASCO Annual Meeting I; Journal of Clinical Oncology, vol. 31, No. 15_suppl, May 2013 (Year: 2013).

\* cited by examiner

ELECTRIC FIELD SHAPING LEADS FOR TREATMENT OF CANCER

This application claims the benefit of U.S. Provisional Application No. 62/575,687, filed Oct. 23, 2017, the content of which is herein incorporated by reference in its entirety.

FIELD

Embodiments herein relate to medical devices including electric field shaping leads and methods for using the same to treat cancerous tumors within a bodily tissue. More specifically, embodiments herein relate to using electric field generating leads configured to generate therapeutic electric fields at the site of a cancerous tumor.

BACKGROUND

According to the American Cancer Society, cancer accounts for nearly 25% of the deaths that occur in the United States each year. The current standard of care for cancerous tumors can include first-line therapies such as surgery, radiation therapy, and chemotherapy. Additional second-line therapies can include radioactive seeding, cryotherapy, hormone or biologics therapy, ablation, and the like. Combinations of first-line therapies and second-line therapies can also be a benefit to patients if one particular therapy on its own is not effective.

Cancerous tumors can form if one normal cell in any part of the body mutates and then begins to grow and multiply too much and too quickly. Cancerous tumors can be a result of a genetic mutation to the cellular DNA or RNA that arises during cell division, an external stimulus such as ionizing or non-ionizing radiation, exposure to a carcinogen, or a result of a hereditary gene mutation. Regardless of the etiology, many cancerous tumors are the result of unchecked rapid cellular division.

Mitosis is the process of cellular division that is a part of the cell cycle for all somatic cells in the body, including many types of cancerous cells. Mitosis includes four basic phases: prophase, metaphase, anaphase, and telophase. Just prior to prophase, a cell will copy its chromosomes to create two identical sister chromatids. During prophase, the chromosomes start to condense and the nuclear membrane surrounding the nucleus disappears. The mitotic spindle also begins to form during prophase. The mitotic spindle includes a self-organized bipolar array of microtubules and centrosomes. Microtubules are generally formed from the polymerization of the highly polar alpha-tubulin and beta-tubulin proteins. Centrosomes are similarly protein-based organelles, two of which migrate to opposite sides of the dividing cell at this phase. The negatively charged end of the microtubules attach to the centrosomes. The positively charged end of the microtubules radiate toward the equator of the dividing cell where they eventually attach to a kinetochore of each sister chromatid. Metaphase can be defined by all chromosomes being aligned at the equator of the dividing cell and bound in the mitotic spindle. An equal number of sister chromatids are then pulled toward opposite ends of the cell during anaphase. Once all chromosomes have been separated, the process of telophase begins, where the cell membrane begins to form a cleavage furrow between the two newly forming sister cells, and cell division becomes complete once the cells physically separate from one another in a process called cytokinesis.

SUMMARY

Embodiments herein include relate to medical devices including electric field shaping leads and methods for using the same to treat cancerous tumors within a bodily tissue. In a first aspect, an implantable lead for a cancer treatment system is provided. The implantable lead can include a lead body having a proximal end and a distal end, where the lead body defines a lumen. The implantable lead can also include a paddle disposed at the distal end of the lead body, the paddle having a width that is greater than a width of the lead body. The implantable lead can include one or more electrodes disposed on the paddle and one or more electrical conductors disposed within the lumen of the lead body to provide electrical communication between the one or more electrodes and the proximal end of the lead body.

In a second aspect, in addition to one or more of the preceding or following aspects, or in the alternative to some aspects, the implantable lead can include from 2 to 36 electrodes disposed on the paddle.

In a third aspect, in addition to one or more of the preceding or following aspects, or in the alternative to some aspects, the implantable lead can include electrodes arranged in a grid pattern on the paddle.

In a fourth aspect, in addition to one or more of the preceding or following aspects, or in the alternative to some aspects, the implantable lead can be configured to implement a switching mechanism to change which electrodes are currently in electrical communication with the proximal end of the lead body.

In a fifth aspect, in addition to one or more of the preceding or following aspects, or in the alternative to some aspects, the implantable lead can include a paddle having a concave portion.

In a sixth aspect, in addition to one or more of the preceding or following aspects, or in the alternative to some aspects, the implantable lead can include a paddle having a first side configured to face a cancerous tumor and a second side opposite the first side, where one or more electrodes are disposed on the first side.

In a seventh aspect, in addition to one or more of the preceding or following aspects, or in the alternative to some aspects, a method of treating a cancerous tumor is provided. The method can include implanting a lead within a patient, the lead including a lead body having a proximal end and a distal end and defining a lumen. The lead can include a paddle disposed at the distal end of the lead body, the paddle having a width that is greater than a width of the lead body. The lead can also include one or more electrodes disposed on the paddle and one or more electrical conductors disposed within the lumen of the lead body to provide electrical communication between the one or more electrodes and the proximal end of the lead body. The method can also include generating one or more electric fields at or near the site of a cancerous tumor from the one or more electrodes.

In an eight aspect, in addition to one or more of the preceding or following aspects, or in the alternative to some aspects, a lead for a cancer treatment system is provided. The lead can include a lead body having a proximal end and a distal end. The lead body can include a patch disposed at the distal end of the lead body, the patch having a width that is greater than the width of the lead body. The patch can be configured to be implanted within a subcutaneous space of a patient. The lead can also include one or more electrodes disposed on the patch and one or more conductors passing through the lead body to provide electrical communication between the one or more electrodes and the proximal end of the lead body.

In a ninth aspect, in addition to one or more of the preceding or following aspects, or in the alternative to some aspects, a method of treating a cancerous tumor is provided.

The method can include implanting one or more patches subcutaneously within a patient, the one or more patches including one or more electrodes disposed thereon and one or more electrical conductors to provide electrical communication with the one or more electrodes. The method can also include generating one or more electric fields at or near the site of a cancerous tumor from the one or more electrodes.

In a tenth aspect, in addition to one or more of the preceding or following aspects, or in the alternative to some aspects, a lead for a cancer treatment system is provided. The lead can include a lead body having a proximal end and a distal end, where the lead body includes one or more electrodes and one or more conductors passing through the lead body to provide electrical communication between the one or more electrodes and the proximal end of the lead body. The lead can also include an insulating material disposed over a portion the one or more electrodes asymmetrically around the diameter of the lead body.

In an eleventh aspect, in addition to one or more of the preceding or following aspects, or in the alternative to some aspects, a method of treating a cancerous tumor is provided. The method can include implanting a lead within a patient, the lead including a lead body having a proximal end and a distal end. The lead body can include one or more electrodes and one or more conductors passing through the lead body to provide electrical communication between the one or more electrodes and the proximal end of the lead body. The lead can also include an insulating material disposed over a portion the one or more electrodes asymmetrically around the diameter of the lead body. The method can also include generating one or more electric fields at or near the site of a cancerous tumor from the one or more electrodes.

In a twelfth aspect, in addition to one or more of the preceding or following aspects, or in the alternative to some aspects, a lead for a cancer treatment system is provided. The lead can include a lead body having a proximal end and a distal end, the lead body including two or more electrodes and one or more conductors passing through the lead body to provide electrical communication between the two or more electrodes and the proximal end of the lead body. The two or more electrodes can be oriented at different positions radially around the outside surface of the lead body.

In a thirteenth aspect, in addition to one or more of the preceding or following aspects, or in the alternative to some aspects, a method of treating a cancerous tumor is provided. The method can include implanting a lead within a patient, the lead including a lead body having a proximal end and a distal end. The lead body can include two or more electrodes and one or more conductors passing through the lead body to provide electrical communication between the two or more electrodes and the proximal end of the lead body. The two or more electrodes can be oriented at different positions radially around the outside surface of the lead body. The method can also include generating one or more electric fields at or near the site of to a cancerous tumor from the two or more electrodes.

In a fourteenth aspect, in addition to one or more of the preceding or following aspects, or in the alternative to some aspects, a lead for a cancer treatment system is provided. The lead can include a lead body having a proximal end and a distal end, the lead body including one or more conductors disposed within the lead body to provide electrical communication. The lead can also include an insulating material disposed over the one or more conductors, the insulating material including one or more first zones and one or more second zones. The thickness of the insulating material over the first zones can be greater than the thickness of the insulating material over the second zones. The second zones can function as electrodes to generate one or more electric fields at or near the site of a cancerous tumor.

In a fifteenth aspect, in addition to one or more of the preceding or following aspects, or in the alternative to some aspects, a method of treating a cancerous tumor is provided. The method can include implanting a lead within a patient, the lead including a lead body having a proximal end and a distal end. The lead body can include one or more conductors disposed within the lead body to provide electrical communication. The lead can also include an insulating material disposed over the one or more conductors, the insulating material including one or more first zones and one or more second zones. The thickness of the insulating material over the first zones can be greater than the thickness of the insulating material over the second zones. The second zones can function as electrodes to generate one or more electric fields at or near the site of a cancerous tumor. The method further including generating one or more electric fields at or near the site of a cancerous tumor from the one or more electrodes.

In a sixteenth aspect, in addition to one or more of the preceding or following aspects, or in the alternative to some aspects, an implantable lead for a cancer treatment system is provided. The implantable lead can include a lead body having a proximal end and a distal end. The lead body can define a lumen and can include a cuff disposed at the distal end of the lead body. The cuff can include an inner surface defining an inner cavity and two or more electrodes disposed on the cuff and arrayed on the inner surface of the cuff. The lead can also include one or more electrical conductors disposed within the lumen of the lead body to provide electrical communication between the two or more electrodes and the proximal end of the lead body.

In a seventeenth aspect, in addition to one or more of the preceding or following aspects, or in the alternative to some aspects, the implantable lead including from 2 to 36 electrodes disposed on the inner surface of the cuff.

In an eighteenth aspect, in addition to one or more of the preceding or following aspects, or in the alternative to some aspects, where the electrodes can be arranged in a grid pattern on the inner surface of the cuff.

In a nineteenth aspect, in addition to one or more of the preceding or following aspects, or in the alternative to some aspects, the implantable lead can be configured to implement a switching mechanism to change which electrodes are currently in electrical communication with the proximal end of the lead body.

In a twentieth aspect, in addition to one or more of the preceding or following aspects, or in the alternative to some aspects, the cuff comprising an elastomeric material.

In a twenty-first aspect, in addition to one or more of the preceding or following aspects, or in the alternative to some aspects, where the cuff can expand in diameter by at 50% without structural failure.

In a twenty-second aspect, in addition to one or more of the preceding or following aspects, or in the alternative to some aspects, the cuff created from a substrate with a plurality of apertures disposed therein.

In a twenty-third aspect, in addition to one or more of the preceding or following aspects, or in the alternative to some aspects, the cuff created from an expandable woven substrate.

In a twenty-fourth aspect, in addition to one or more of the preceding or following aspects, or in the alternative to some aspects, an implantable organ cuff for a cancer treatment system is provided. The implantable organ cuff can include a cuff body, where the cuff body includes an inner surface that defines an inner cavity. The implantable organ cuff can also include two or more electrodes disposed on the cuff body and arrayed on the inner surface of the cuff body and one or more electrical conductors disposed within or on the cuff body in electrical communication between a connection terminus and the two or more electrodes.

In a twenty-fifth aspect, in addition to one or more of the preceding or following aspects, or in the alternative to some aspects, a method of treating a cancerous tumor is provided. The method can include implanting a lead within a patient, the lead including a lead body having a proximal end and a distal end. The lead body can also include a lumen and can include a cuff disposed at the distal end of the lead body. The cuff can include an inner surface defining an inner cavity. The lead can also include two or more electrodes disposed on the cuff and arrayed on the inner surface of the cuff and one or more electrical conductors disposed within the lumen of the lead body to provide electrical communication between the two or more electrodes and the proximal end of the lead body. The method can also include generating one or more electric fields at or near the site of a cancerous tumor from the one or more electrodes.

In a twenty-sixth aspect, in addition to one or more of the preceding or following aspects, or in the alternative to some aspects, a lead for a cancer treatment system is provided. The lead can include a lead body having a proximal end and a distal end. The lead body can include at least two electrodes and one or more conductors passing through the lead body to provide electrical communication between the at least two electrodes and the proximal end of the lead body. The lead can also include an insulating flange disposed circumferentially on an exterior surface of the lead body, the insulating flange made from an insulating material and configured to inter a direct electrical conduction path between the two electrodes.

In a twenty-seventh aspect, in addition to one or more of the preceding or following aspects, or in the alternative to some aspects, the direct electrical conduction path is a straight-line electrical conduction path.

In a twenty-eighth aspect, in addition to one or more of the preceding or following aspects, or in the alternative to some aspects, a lead for a cancer treatment system is provided. The lead can include a lead body having a proximal end and a distal end. The lead body can include a coiled electrode and one or more conductors passing through the lead body to provide electrical communication between the coiled electrode and the proximal end of the lead body. The lead can also include an insulating material disposed over the coiled electrode.

In a twenty-ninth aspect, in addition to one or more of the preceding or following aspects, or in the alternative to some aspects, where the thickness of the insulating material varies along a length of the coiled electrode.

In a thirtieth aspect, in addition to one or more of the preceding or following aspects, or in the alternative to some aspects, where portions of the insulating material are discontinuous creating gaps.

In a thirty-first aspect, in addition to one or more of the preceding or following aspects, or in the alternative to some aspects, a method of treating a cancerous tumor is provided. The method can include implanting a lead within a patient, the lead including a lead body having a proximal end and a distal end. The lead body can include a coiled electrode and one or more conductors passing through the lead body to provide electrical communication between the coiled electrode and the proximal end of the lead body. The lead can also include an insulating material disposed over the coiled electrode. The method can also include generating one or more electric fields at or near the site of a cancerous tumor from the one or more electrodes.

In a thirty-second aspect, in addition to one or more of the preceding or following aspects, or in the alternative to some aspects, where the coiled electrode is implanted subcutaneously.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

As referenced above, many cancerous tumors can result from unchecked rapid cellular division. Some traditional first-line therapies to treat cancerous tumors can include surgery, radiation therapy, and chemotherapy. However, many first-line therapies have undesirable concomitant side effects, such as fatigue, hair loss, immunosuppression, and long surgical recovery times, to name a few.

While not intending to be bound by theory, it is believed that alternating electric fields can disrupt mitosis within a cancerous tumor by interfering with the dipole alignment of key proteins involved in cellular division; tubulin and septin in particular. The polymerization of tubulin proteins that form microtubule spindle fibers can be disrupted, thus preventing the formation of spindle fibers required for chromosome separation. This can halt cellular division at the metaphase stage of mitosis. In some instances, an alternating electric field can halt polymerization of already growing spindle fibers, leading to incomplete spindles and unequal chromosome separation during anaphase, should the cell survive that long. In each case, halting microtubule spindle formation and unequal chromosome separation during anaphase caused by incomplete polymerization of microtubules can result in apoptosis (i.e., programmed cell death).

It is also believed that alternating electric fields can lead to increased electric field density near the cleavage furrow of the dividing cells during telophase. An increased electric field density in the region of the cleavage furrow can result in dielectrophoresis of charged macromolecules, such as proteins and nucleic acids, toward the high electric field density at the furrow. The unequal concentration of key macromolecules required for cellular division at the site of the cleavage furrow can disrupt the final separation of the sister cells during telophase and eventually lead to apoptosis.

The shape and size of an electric field can be modulated by the positioning of electrodes in space and by varying the electric field at a number of different electrode configurations. Sometimes, the shape of an electric field can be manipulated by alternating or switching the polarity of discrete electrodes within an individual array of electrodes or within the entire medical device system.

Figure 1:
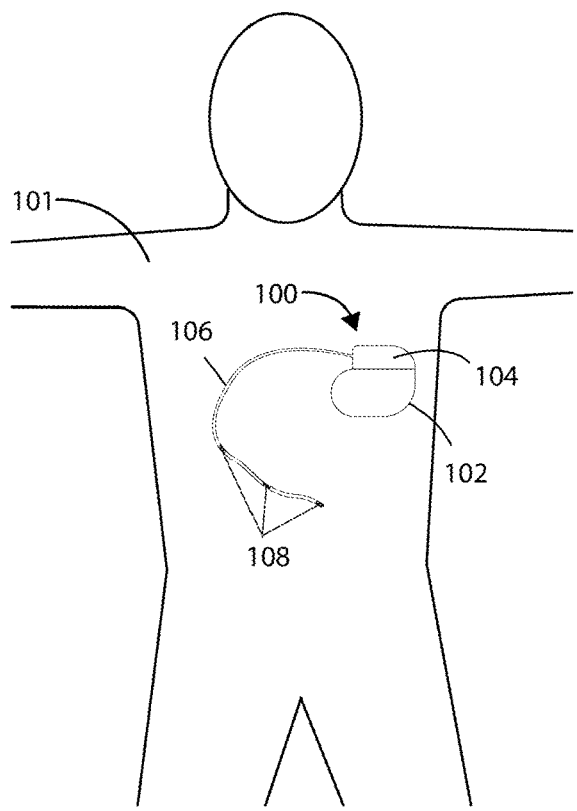
FIG. 1 is a schematic view of a medical system in accordance with various embodiments herein.

Referring now to FIG. 1, a schematic view is shown of a medical device 100 in accordance with various embodiments herein. The medical device 100 can be implanted entirely within the body of a patient 101 at or near the site of a cancerous tumor located within a bodily tissue. Various implant sites can be used including areas such as in the limbs, the upper torso, the abdominal area, the head, and the like.

Figure 2:
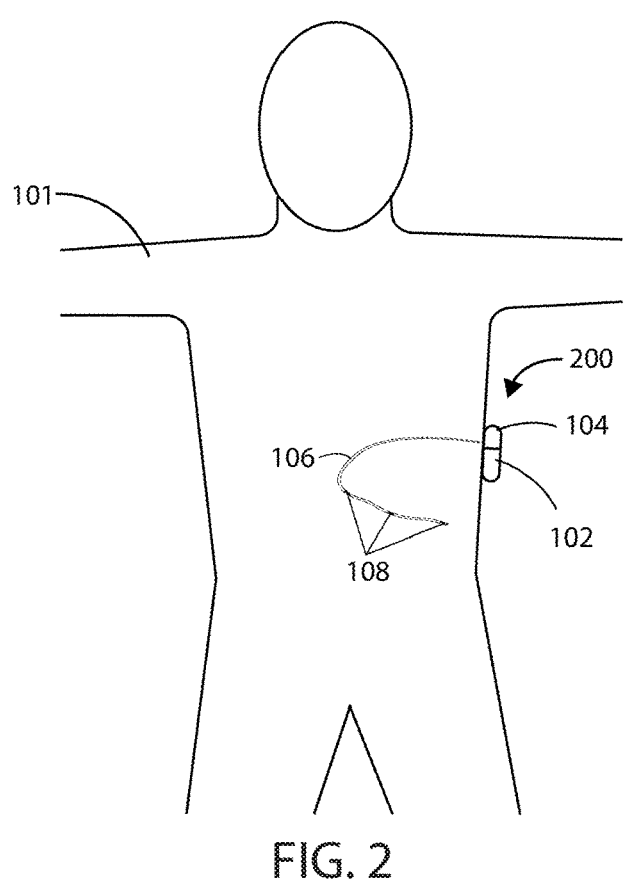
FIG. 2 is a schematic view of a medical system in accordance with various embodiments herein.

Referring now to FIG. 2, another schematic view is shown of a medical device 200 in accordance with various embodiments herein. The medical device 200 can be partially implanted within the body of a patient 101. In some embodiments, the medical device can be partially implanted and partially external to the body of a patient. In other embodiments, a partially implanted medical device can include a transcutaneous connection between components disposed internal to the body and external to the body. A partially implanted medical device can wirelessly communicate with a partially external portion of a medical device over a wireless connection.

In some embodiments, a portion of the medical device can be entirely implanted and a portion of the medical device can be entirely external. For example, in some embodiments, one or more electrodes or leads can be entirely implanted within the body, whereas the portion of the medical device that generates an electric field, such as an electric field generator, can be entirely external to the body. It will be appreciated that in some embodiments described herein, the electric field generators described can include the many of the same components as and can be configured to perform many of the same functions as a pulse generator. In embodiments where a portion of a medical device is entirely implanted and a portion of the medical device is entirely external, the portion of the medical device that is entirely external can communicate wirelessly with the portion of the medical device that is entirely internal. However, in other embodiments a wired connection can be used.

The medical device 100 or medical device 200 can include a housing 102 and a header 104 coupled to the housing 102. Various materials can be used. However, in some embodiments, the housing 102 can be formed of a material such as a metal, ceramic, polymer, composite, or the like. In some embodiments, the housing 102, or one or more portions thereof, can be formed of titanium. The header 104 can be formed of various materials, but in some embodiments the header 104 can be formed of a translucent polymer such as an epoxy material. In some embodiments the header 104 can be hollow. In other embodiments the header 104 can be filled with components and/or structural materials such as epoxy or another material such that it is non-hollow.

In some embodiments where a portion of the medical device 100 or 200 is partially external, the header 104 and housing 102 can be surrounded by a protective casing made of durable polymeric material. In other embodiments, where a portion of the medical device 100 or 200 is partially external, the header 104 and housing 102 can be surrounded by a protective casing made of a combination of polymeric material, metallic material, and/or glass material.

The header 104 can be coupled to one or more leads 106. The header 104 can serve to provide fixation of the proximal end of one or more leads 106 and electrically couple the one or more leads 106 to one or more components within the housing 102. The one or more leads 106 can include one or more electrodes 108 disposed along the length of the electrical leads 106. In some embodiments, electrodes 108 can include electric field generating electrodes and in other embodiments electrodes 108 can include electric field sensing electrodes. In some embodiments, leads 106 can include both electric field generating and electric field sensing electrodes. In other embodiments, leads 106 can include any number of electrodes that are both electric field sensing and electric field generating. It will be appreciated that while many embodiments of medical devices herein are designed to function with leads, leadless medical devices that generate electrical fields are also contemplated herein.

Figure 3:
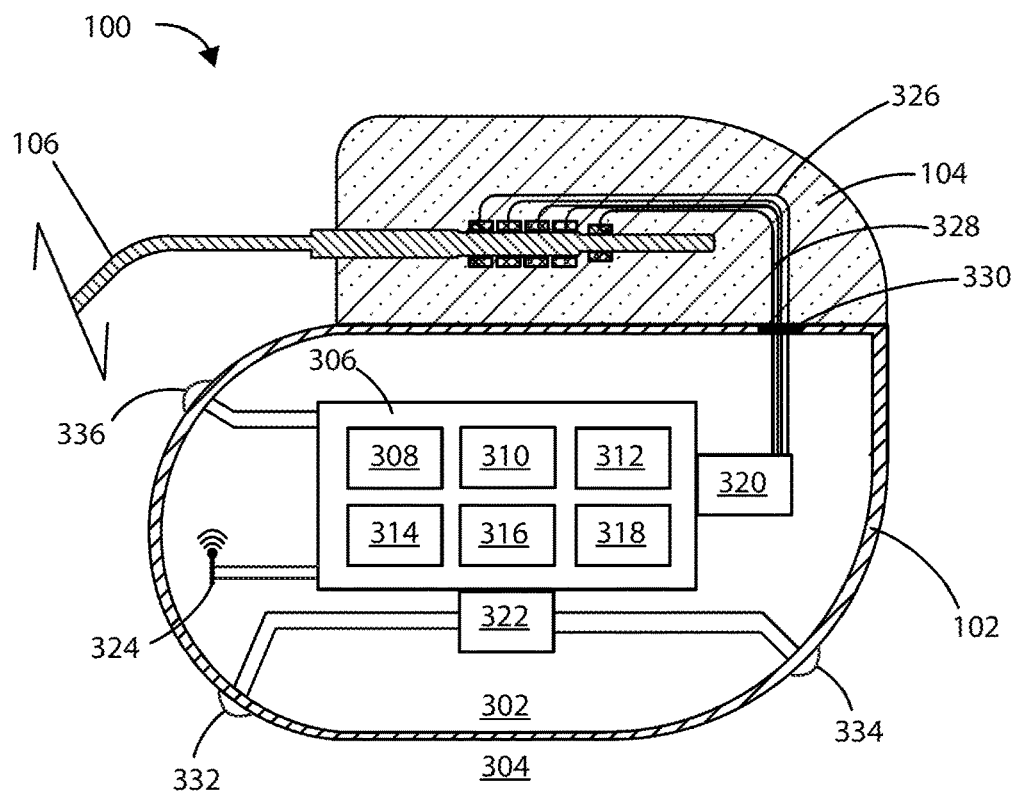
FIG. 3 is a schematic cross-sectional view of a medical device in accordance with various embodiments herein.

Referring now to FIG. 3, a schematic cross-sectional view of medical device 100 is shown in accordance with various embodiments herein. Housing 102 can define an interior volume 302 that can be hollow and that in some embodiments is hermetically sealed off from the area 304 outside of medical device 100. In other embodiments the housing 102 can be filled with components and/or structural materials such that it is non-hollow. The medical device 100 can include control circuitry 306, which can include various components 308, 310, 312, 314, 316, and 318 disposed within housing 102. In some embodiments, these components can be integrated and in other embodiments these components can be separate. In yet other embodiments, there can be a combination of both integrated and separate components. The medical device 100 can also include an antenna 324, to allow for unidirectional or bidirectional wireless data communication. In some embodiments, the components of medical device 100 can include an inductive energy receiver coil (not shown) communicatively coupled or attached thereto to facilitate transcutaneous recharging of the medical device via recharging circuitry.

The various components 308, 310, 312, 314, 316, and 318 of control circuitry 306 can include, but are not limited to, a microprocessor, memory circuit (such as random access memory (RAM) and/or read only memory (ROM)), recorder circuitry, controller circuit, a telemetry circuit, a power supply circuit (such as a battery), a timing circuit, and an application specific integrated circuit (ASIC), a recharging circuit, amongst others. Control circuitry 306 can be in communication with an electric field generating circuit 320 that can be configured to generate electric current to create one or more fields. The electric field generating circuit 320 can be integrated with the control circuitry 306 or can be a separate component from control circuitry 306. Control circuitry 306 can be configured to control delivery of electric current from the electric field generating circuit 320. In some embodiments, the electric field generating circuit 320 can be present in a portion of the medical device that is external to the body.

In some embodiments, the control circuitry 306 can be configured to direct the electric field generating circuit 320 to deliver an electric field using one or more frequencies selected from a range of between 10 kHz to 1 MHz. In some embodiments, the control circuitry 306 can be configured to direct the electric field generating circuit 320 to deliver an electric field at one or more frequencies selected from a range of between 100 kHz to 500 kHz. In some embodiments, the control circuitry 306 can be configured to direct the electric field generating circuit 320 to deliver an electric field at one or more frequencies selected from a range of between 100 kHz to 300 kHz. In some embodiments, the control circuitry 306 can be configured to direct the electric field generating circuit 320 to periodically deliver an electric field using one or more frequencies greater than 1 MHz.

In some embodiments, the electric field can be effective in disrupting cellular mitosis in cancerous cells. The electric field can be delivered to the site of a cancerous tumor along more than one vector. In some examples, the electric field can be delivered along at least one vector, including at least one of the lead electrodes. In some embodiments, at least two vectors with spatial diversity between the two vectors can be used. The vectors can be spatially separated (e.g., the vectors can be disposed at an angle with respect to one another) by at least about 10, 20, 30, 40, 50, 60, 70, 80 or 90 degrees.

A desired electric field strength can be achieved by delivering an electric current between two electrodes. The specific current and voltage at which the electric field is delivered can vary and can be adjusted to achieve the desired electric field strength at the site of the tissue to be treated. In some embodiments, the control circuitry 306 can be configured to direct the electric field generating circuit 320 to deliver an electric field using currents ranging from 1 mAmp to 1000 mAmp to the site of a cancerous tumor. In some embodiments, the control circuitry 306 can be configured to direct the electric field generating circuit 320 to deliver an electric field using currents ranging from 20 mAmp to 500 mAmp to the site of a cancerous tumor. In some embodiments, the control circuitry 306 can be configured to direct the electric field generating circuit 320 to deliver an electric field using currents ranging from 30 mAmp to 300 mAmp to the site of a cancerous tumor.

In some embodiments, the control circuitry 306 can be configured to direct the electric field generating circuit 320 to deliver an electric field using currents including 1 mAmp, 2 mAmp, 3 mAmp, 4 mAmp, 5 mAmp, 6 mAmp, 7 mAmp, 8 mAmp, 9 mAmp, 10 mAmp, 15 mAmp, 20 mAmp, 25 mAmp, 30 mAmp, 35 mAmp, 40 mAmp, 45 mAmp, 50 mAmp, 60 mAmp, 70 mAmp, 80 mAmp, 90 mAmp, 100 mAmp, 125 mAmp, 150 mAmp, 175 mAmp, 200 mAmp, 225 mAmp, 250 mAmp, 275 mAmp, 300 mAmp, 325 mAmp, 350 mAmp, 375 mAmp, 400 mAmp, 425 mAmp, 450 mAmp, 475 mAmp, 500 mAmp, 525 mAmp, 550 mAmp, 575 mAmp, 600 mAmp, 625 mAmp, 650 mAmp, 675 mAmp, 700 mAmp, 725 mAmp, 750 mAmp, 775 mAmp, 800 mAmp, 825 mAmp, 850 mAmp, 875 mAmp, 900 mAmp, 925 mAmp, 950 mAmp, 975 mAmp, or 1000 mAmp. It will be appreciated that the control circuitry can be configured to direct the electric field generating circuit 320 to deliver an electric field at a current falling within a range, wherein any of the forgoing currents can serve as the lower or upper bound of the range, provided that the lower bound of the range is a value less than the upper bound of the range.

In some embodiments, the control circuitry 306 can be configured to direct the electric field generating circuit 320 to deliver an electric field using voltages ranging from 1 $V_{rms}$ to 50 $V_{rms}$ to the site of a cancerous tumor. In some embodiments, the control circuitry 306 can be configured to direct the electric field generating circuit 320 to deliver an electric field using voltages ranging from 5 $V_{rms}$ to 30 $V_{rms}$ to the site of a cancerous tumor. In some embodiments, the control circuitry 306 can be configured to direct the electric field generating circuit 320 to deliver an electric field using voltages ranging from 10 $V_{rms}$ to 20 $V_{rms}$ to the site of a cancerous tumor.

In some embodiments, the control circuitry 306 can be configured to direct the electric field generating circuit 320 to deliver an electric field using one or more voltages including 1 $V_{rms}$, 2 $V_{rms}$, 3 $V_{rms}$, 4 $V_{rms}$, 5 $V_{rms}$, 6 $V_{rms}$, 7 $V_{rms}$, 8 $V_{rms}$, 9 $V_{rms}$, 10 $V_{rms}$, 15 $V_{rms}$, 20 $V_{rms}$, 25 $V_{rms}$, 30 $V_{rms}$, 35 $V_{rms}$, 40 $V_{rms}$, 45 $V_{rms}$, or 50 $V_{rms}$. It will be appreciated that the control circuitry can be configured to direct the electric field generating circuit 320 to deliver an electric field using a voltage falling within a range, wherein any of the forgoing voltages can serve as the lower or upper bound of the range, provided that the lower bound of the range is a value less than the upper bound of the range.

In some embodiments, the control circuitry 306 can be configured to direct the electric field generating circuit 320 to deliver and electric field using one or more frequencies including 10 kHz, 20 kHz, 30 kHz, 40 kHz, 50 kHz, 60 kHz, 70 kHz, 80 kHz, 90 kHz, 100 kHz, 125 kHz, 150 kHz, 175 kHz, 200 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, 1 MHz. It will be appreciated that the electric field generating circuit 320 can deliver an electric field using a frequency falling within a range, wherein any of the foregoing frequencies can serve as the upper or lower bound of the range, provided that the upper bound is greater than the lower bound.

In some embodiments, the control circuitry 306 can be configured to direct the electric field generating circuit 320 to generate one or more applied electric field strengths selected from a range of between 0.25 V/cm to 1000 V/cm. In some embodiments, the control circuitry 306 can be configured to direct the electric field generating circuit 320 to generate one or more applied electric field strengths of greater than 3 V/cm. In some embodiments, the control circuitry 306 can be configured to direct the electric field generating circuit 320 to generate one or more applied electric field strengths selected from a range of between 1 V/cm to 10 V/cm. In some embodiments, the control circuitry 306 can be configured to direct the electric field generating circuit 320 to generate one or more applied electric field strengths selected from a range of between 3 V/cm to 5 V/cm.

In other embodiments, the control circuitry 306 can be configured to direct the electric field generating circuit 320 to generate one or more applied electric field strengths including 0.25 V/cm, 0.5 V/cm, 0.75 V/cm, 1.0 V/cm, 2.0 V/cm, 3.0 V/cm, 5.0 V/cm, 6.0 V/cm, 7.0 V/cm, 8.0 V/cm, 9.0 V/cm, 10.0 V/cm, 20.0 V/cm, 30.0 V/cm, 40.0 V/cm, 50.0 V/cm, 60.0 V/cm, 70.0 V/cm, 80.0 V/cm, 90.0 V/cm, 100.0 V/cm, 125.0 V/cm, 150.0 V/cm, 175.0 V/cm, 200.0 V/cm, 225.0 V/cm, 250.0 V/cm, 275.0 V/cm, 300.0 V/cm, 325.0 V/cm, 350.0 V/cm, 375.0 V/cm, 400.0 V/cm, 425.0 V/cm, 450.0 V/cm, 475.0 V/cm, 500.0 V/cm, 600.0 V/cm, 700.0 V/cm, 800.0 V/cm, 900.0 V/cm, 1000.0 V/cm. It will be appreciated that the electric field generating circuit 320 can generate an electric field having a field strength at a treatment site falling within a range, wherein any of the foregoing field strengths can serve as the upper or lower bound of the range, provided that the upper bound is greater than the lower bound.

In some embodiments, the control circuitry 306 can be configured to direct the electric field generating circuit 320 to deliver an electric field via leads 106 to the site of a cancerous tumor located within a bodily tissue. In other embodiments, the control circuitry 306 can be configured to direct the electric field generating circuit 320 to deliver an electric field via the housing 102 of medical device 100 to the site of a cancerous tumor located within a bodily tissue. In other embodiments, the control circuitry 306 can be configured to direct the electric field generating circuit 320 to deliver an electric field between leads 106 and the housing 102 of medical device 100. In some embodiments, one or more leads 106 can be in electrical communication with the electric field generating circuit 320. In some embodiments, the one or more leads 106 can include one or more electrodes 108 disposed along the length of the leads 106, where the electrodes 108 can be in electrical communication with the electric field generating circuit 320.

In some embodiments, various components within medical device 100 can include an electric field sensing circuit 322 configured to generate a signal corresponding to sensed electric fields. Electric field sensing circuit 322 can be integrated with control circuitry 306 or it can be separate from control circuitry 306.

Sensing electrodes can be disposed on or adjacent to the housing of the medical device, on one or more leads connected to the housing, on a separate device implanted near or in the tumor, or any combination of these locations. In some embodiments, the electric field sensing circuit 322 can include a first sensing electrode 332 and a second sensing electrode 334. In other embodiments, the housing 102 itself can serve as a sensing electrode for the electric field sensing circuit 322. The electrodes 332 and 334 can be in communication with the electric field sensing circuit 322. The electric field sensing circuit 322 can measure the electrical potential difference (voltage) between the first electrode 332 and the second electrode 334. In some embodiments, the electric field sensing circuit 322 can measure the electrical potential difference (voltage) between the first electrode 332 or second electrode 334, and an electrode disposed along the length of one or more leads 106. In some embodiments, the electric field sensing circuit can be configured to measure sensed electric fields and to record electric field strength in V/cm.

It will be appreciated that the electric field sensing circuit 322 can additionally measure an electrical potential difference between the first electrode 332 or the second electrode 334 and the housing 102 itself In other embodiments, the medical device can include a third electrode 336, which can be an electric field sensing electrode or an electric field generating electrode. In some embodiments, one or more sensing electrodes can be disposed along lead 106 and can serve as additional locations for sensing an electric field. Many combinations can be imagined for measuring electrical potential difference between electrodes disposed along the length of one or more leads 106 and the housing 102 in accordance with the embodiments herein.

In some embodiments, the one or more leads 106 can be in electrical communication with the electric field generating circuit 320. The one or more leads 106 can include one or more electrodes 108, as shown in FIGS. 1 and 2. In some embodiments, various electrical conductors, such as electrical conductors 326 and 328, can pass from the header 104 through a feed-through structure 330 and into the interior volume 302 of medical device 100. As such, the electrical conductors 326 and 328 can serve to provide electrical communication between the one or more leads 106 and control circuitry 306 disposed within the interior volume 302 of the housing 102.

In some embodiments, recorder circuitry can be configured to record the data produced by the electric field sensing circuit 322 and record time stamps regarding the same. In some embodiments, the control circuitry 306 can be hardwired to execute various functions, while in other embodiments the control circuitry 306 can be directed to implement instructions executing on a microprocessor or other external computation device. A telemetry circuit can also be provided for communicating with external computation devices such as a programmer, a home-based unit, and/or a mobile unit (e.g. a cellular phone, personal computer, smart phone, tablet computer, and the like).

Figure 4:
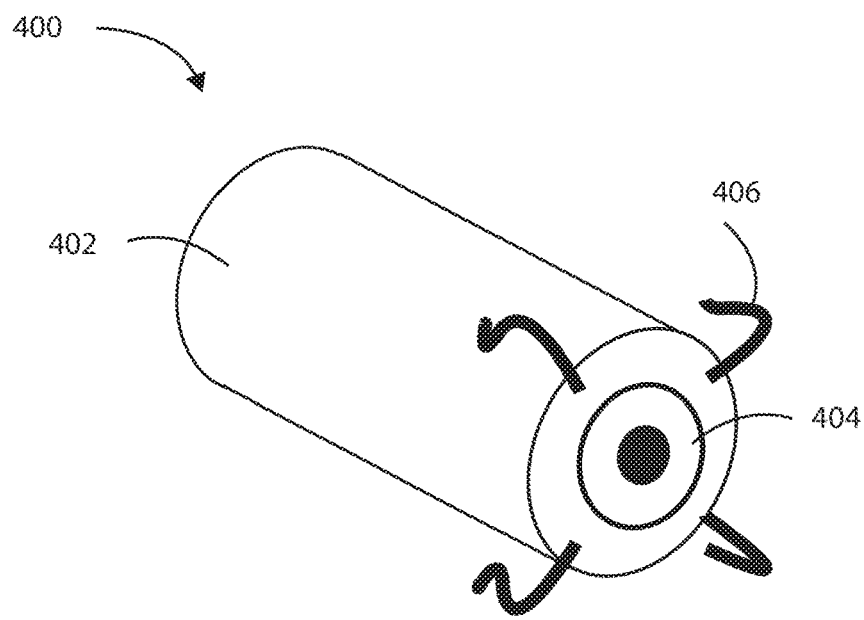
FIG. 4 is a schematic view of a medical device in accordance with various embodiments herein.

Referring now to FIG. 4, leadless medical device 400 is shown in accordance with the embodiments herein. The leadless medical device 400 can include a housing 402 and a header 404 coupled to the housing 402. Various materials can be used. However, in some embodiments, the housing 402 can be formed of a material such as a metal, ceramic, polymer, composite, or the like. In some embodiments, the housing 402, or one or more portions thereof, can be formed of titanium. The header 404 can be formed of various materials, but in some embodiments the header 404 can be formed of a translucent polymer such as an epoxy material. In some embodiments the header 404 can be hollow. In other embodiments the header 404 can be filled with components and/or structural materials such as epoxy or another material such that it is non-hollow. In some embodiments, leadless medical device 400 can include fixation elements 406 to keep a leadless medical device 400 positioned at or near the site of a cancerous tumor within the body. In some embodiments, fixation elements 406 can include talons, tines, helices, bias, and the like.

Figure 5:
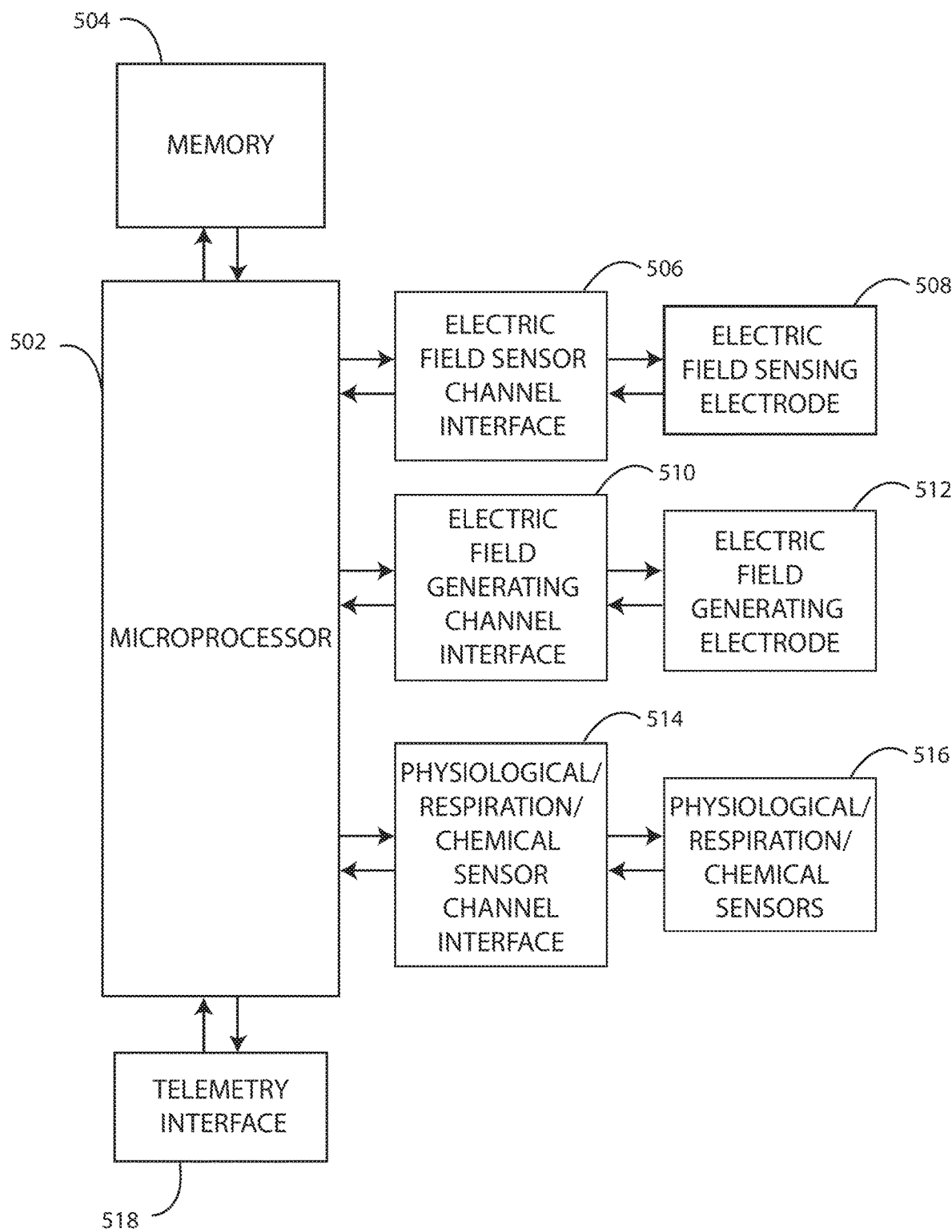
FIG. 5 is a schematic diagram of components of a medical device in accordance with various embodiments herein.

Elements of various embodiments of the medical devices described herein are shown in FIG. 5. However, it will be appreciated that some embodiments can include additional elements beyond those shown in FIG. 5. In addition, some embodiments may lack some elements shown in FIG. 5. The medical devices as embodied herein can gather information through one or more sensing channels and can output information through one or more field generating channels.

A microprocessor 502 can communicate with a memory 504 via a bidirectional data bus. The memory 504 can include read only memory (ROM) or random access memory (RAM) for program storage and RAM for data storage. The microprocessor 502 can also be connected to a telemetry interface 518 for communicating with external devices such as a programmer, a home-based unit and/or a mobile unit (e.g. a cellular phone, personal computer, smart phone, tablet computer, and the like) or directly to the cloud or another communication network as facilitated by a cellular or other data communication network. In some embodiments, the medical device can include an inductive energy receiver coil interface (not shown) communicatively coupled or attached thereto to facilitate transcutaneous recharging of the medical device.

The medical device can include one or more electric field sensing electrodes 508 and one or more electric field sensor channel interfaces 506 that can communicate with a port of microprocessor 502. The medical device can also include one or more electric field generating electrodes 512 and one or more electric field generating channel interfaces 510 that can communicate with a port of microprocessor 502. The medical device can also include one or more physiological sensors, respiration sensors, or chemical sensors 516 and one or more physiological/respiration/chemical sensor channel interfaces 514 that can communicate with a port of microprocessor 502. The channel interfaces 506, 510, and 514 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like.

In some embodiments, the physiological sensors can include sensors that monitor temperature, blood flow, blood pressure, and the like. In some embodiments, the respiration sensors can include sensors that monitor respiration rate, respiration peak amplitude, and the like. In some embodiments, the chemical sensors can measure the quantity of an analyte present in a treatment area about the sensor, including but not limited to analytes such as of blood urea nitrogen, creatinine, fibrin, fibrinogen, immunoglobulins, deoxyribonucleic acids, ribonucleic acids, potassium, sodium, chloride, calcium, magnesium, lithium, hydronium, hydrogen phosphate, bicarbonate, and the like. However, many other analytes are also contemplated herein. Exemplary chemical/analyte sensors are disclosed in commonly owned U.S. Pat. No. 7,809,441 to Kane et al., and which is hereby incorporated by reference in its entirety.

Although the physiological, respiration, or chemical sensors 516 are shown as part of a medical device in FIG. 5, it is realized that in some embodiments one or more of the physiological, respiration, or chemical sensors could be physically separate from the medical device. In various embodiments, one or more of the physiological, respiration, or chemical sensors can be within another implanted medical device communicatively coupled to a medical device via telemetry interface 518. In yet other embodiments, one or more of the physiological, respiration, or chemical sensors can be external to the body and coupled to a medical device via telemetry interface 518.

Figure 6:
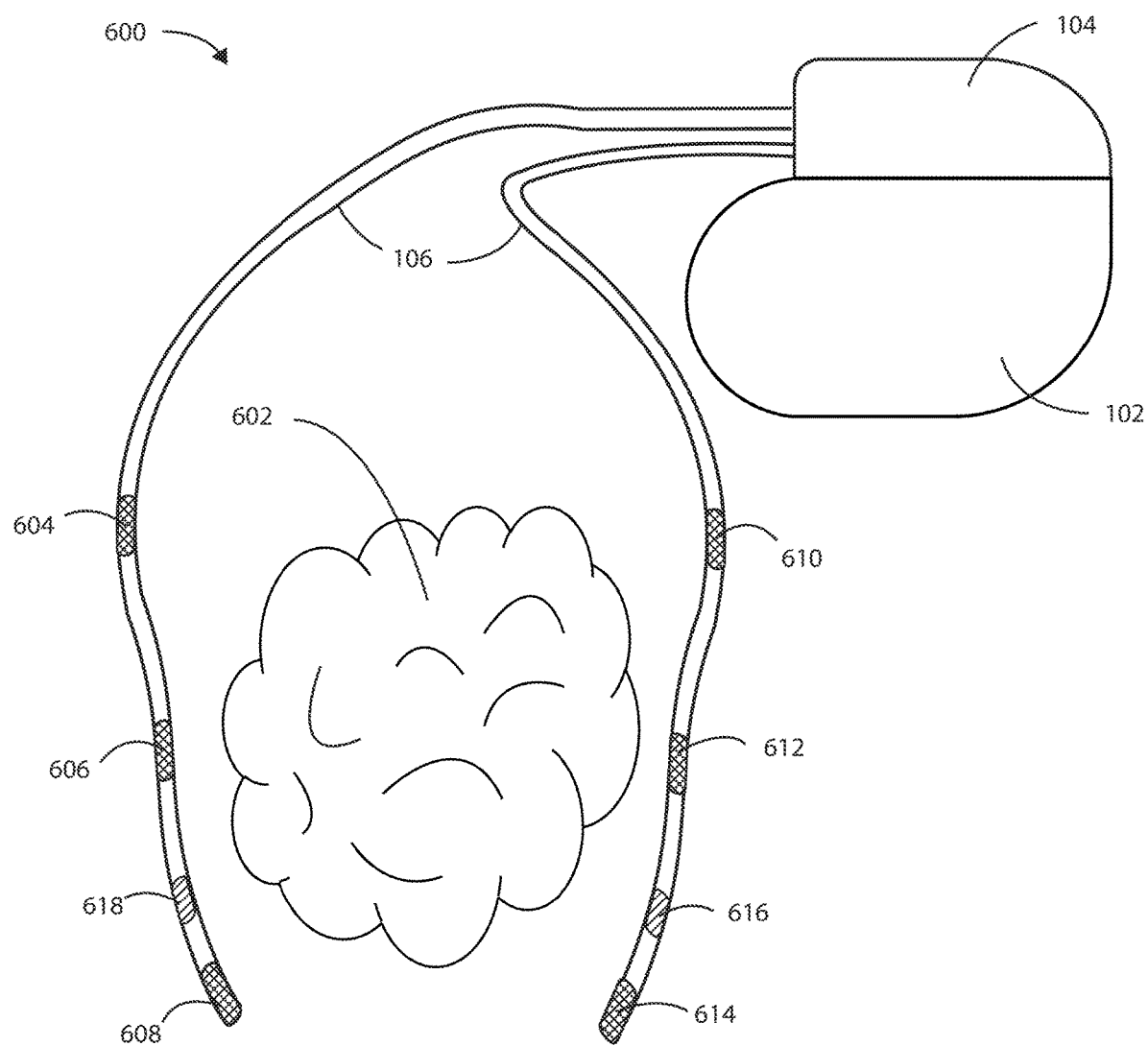
FIG. 6 is a schematic view of a medical device in accordance with various embodiments herein.

Referring now to FIG. 6, a schematic diagram of a medical device 600 is shown in accordance with the embodiments herein. Medical device 600 can include housing 102 and header 104, and one or more leads 106. Leads 106 can include one or more electrodes such as electrodes 604, 606, 608, 610, 612, or 614 disposed along the length of the leads 106. In some embodiments, electrodes 604, 606, 608, 610, 612, or 614 can include electric field generating electrodes and in other embodiments electrodes 604, 606, 608, 610, 612, or 614 can include electric field sensing electrodes. In some embodiments, leads 106 can include both electric field generating and electric field sensing electrodes.

The proximal ends of leads 106 are disposed within the header 104. The distal ends of electrical leads 106 can surround a cancerous tumor 602 such that the electrodes 604, 606, 608, 610, 612, or 614 are brought into proximity of the cancerous tumor 602. In some embodiments, the leads 106 can be positioned within the vasculature such that electrodes 604, 606, 608, 610, 612, or 614 are adjacent to or positioned within the cancerous tumor 602. However, it will be appreciated that leads 106 can be disposed in various places within or around the cancerous tumor 602. In some embodiments, the leads 106 can pass directly through the cancerous tumor 602.

In some embodiments, the leads 106 can include one or more tracking markers 616 or 618 along the length of the lead for use in determining the precise location of the electrodes relative to the tumor. In some embodiments, the one or more tracking markers can be disposed directly distal or directly proximal to the one or more electrodes disposed on the lead. In some embodiments, the tracking markers can be formed from a magnetic material. In some embodiments, the tracking markers can be formed from a radiographic material. In some embodiments, the tracking markers can be formed from a fluorographic material.

It will be appreciated that a plurality of electric field vectors can be generated between various combinations of electrodes 604, 606, 608, 610, 612, or 614 disposed along leads 106 to create an electric field. For example, one or more electric field vectors can be generated between electrodes 604 and 610. Similarly, one or more electric field vectors can be generated between electrodes 606 and 612. It will also be appreciated that one or more electric field vectors can be generated between any combination of electrodes 604, 606, 608, 610, 612, or 614. In some embodiments, one or more electric field vectors can be generated between any combination of electrodes 604, 606, 608, 610, 612, or 614 and the housing 102 of medical device 400. It will be appreciated that one or more unipolar or multipolar leads can be used in accordance with the embodiments herein. In some embodiments, a combination of unipolar and multipolar leads can be used. In other embodiments, a circular lead, clamp lead, cuff lead, paddle lead, or patch lead can be used.

Figure 7:
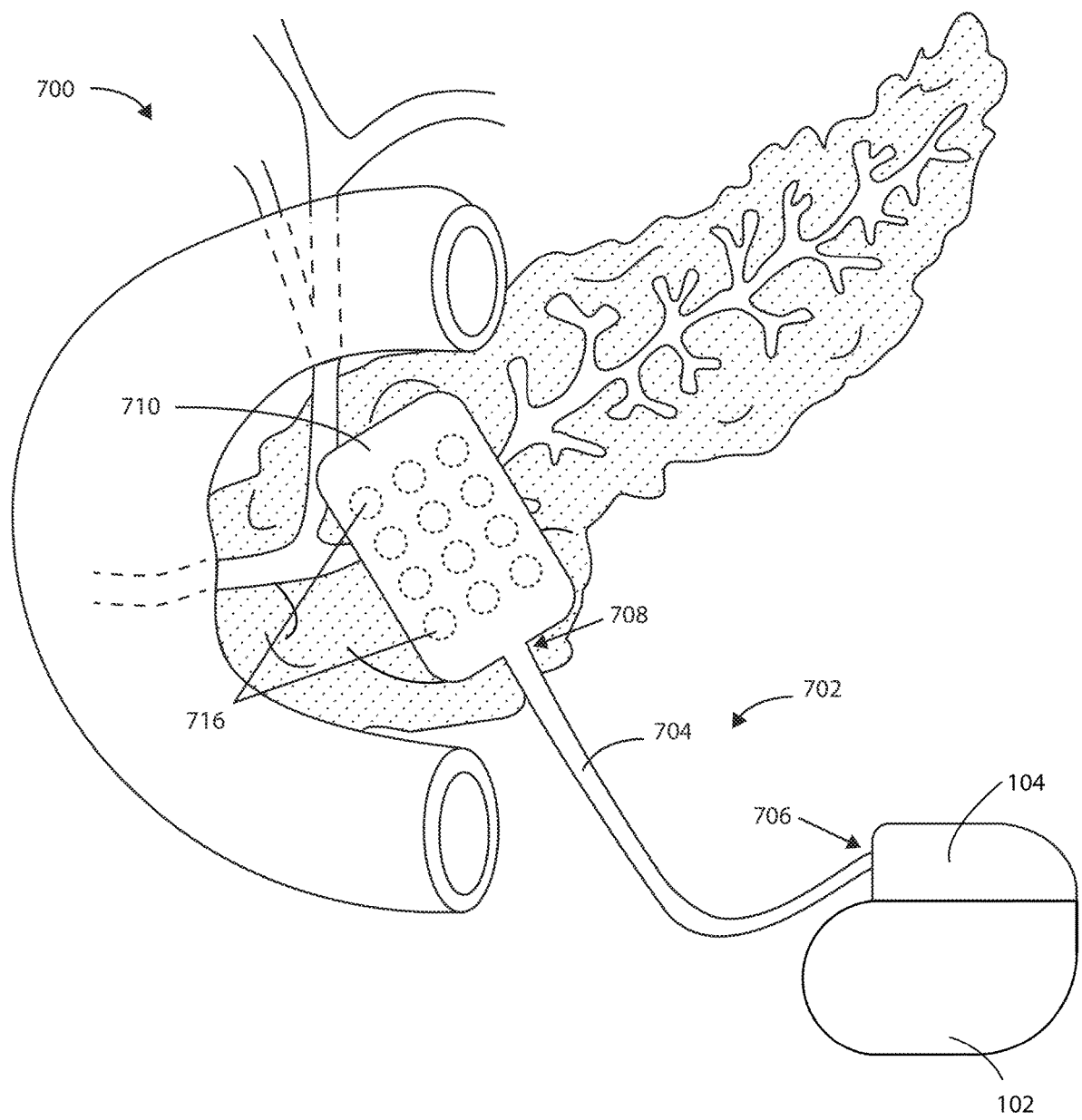
FIG. 7 is a schematic view of a medical device in accordance with various embodiments herein.

Referring now to FIG. 7 (not shown to scale), lead 702 for use in a cancer treatment system 700 is shown in accordance with various embodiments herein. It will be appreciated that cancer treatment system 700 is shown in the context of providing treatment to a site of a cancerous tumor at or near the pancreas, but cancer treatment system 700 can be implanted at any suitable location within the body. Cancer treatment system 700 can include one or more leads 702 for delivering a cancer treatment. The leads 702 can include a lead body 704 having a proximal end 706 and a distal end 708, where the lead body 704 can define a lumen (not shown). The lead body 704 can include a paddle 710 disposed at the distal end 708 of the lead body 704. Fixation of the paddle 710 to an organ and/or tumor site can be achieved by a suture, staple, talon, glue, and the like. There can be one or more electrodes 716 disposed on the paddle 710. There can be one or more electrical conductors (not shown) disposed within the lumen of the lead body 704 to provide electrical communication between the one or more electrodes 716 and the proximal end 706 of the lead body 704.

Electric fields can be generated between any combinations of electrodes 716 disposed on paddle 710. In some embodiments, electric fields can be generated between any combinations of electrodes 716 disposed on two or more paddles 710. In some embodiments, electric fields can be generated between any combinations of electrodes 716 disposed on one or more paddles 710 and the housing 102 of a medical device. In other embodiments, electric fields can be generated between any combinations of electrodes 716 disposed on one or more paddles 710 and one or more additional leads, such as any of the other lead configurations disclose herein, having electrodes disposed thereon and placed at the site of a cancerous tumor. In some embodiments, the electrodes 716 can be field generating electrodes or field sensing electrodes.

In some embodiments, the one or more leads 702 can include anywhere from 2 to 36 electrodes 716 disposed on the paddle 710. In some embodiments, the one or more leads 702 can include anywhere from 2 to 50 electrodes 716 disposed on the paddle 710. In some embodiments, the one or more leads 702 can include anywhere from 3 to 12 electrodes 716 disposed on the paddle 710. In some embodiments, the one or more leads 702 can include anywhere from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 electrodes 716 disposed on the paddle 710. It will be appreciated that the one or more leads 702 can include any number of electrodes falling within a range, wherein any of the foregoing numbers of electrodes can serve as the upper or lower bound of the range, provided that the upper bound is greater than the lower bound.

In some embodiments, the shape of the electric field can be influenced by the placement of the electrodes 716 on the paddle 710 and/or by the shape of the paddle 710. In some embodiments, the electrodes 716 can be arranged in a grid pattern on the paddle 710. In other embodiments, the electrodes 716 can be arranged in a circular array on the paddle 710. In some embodiments, the paddle 710 can include a concave portion. In other embodiments, the paddle 710 can include a convex portion.

Figure 8:
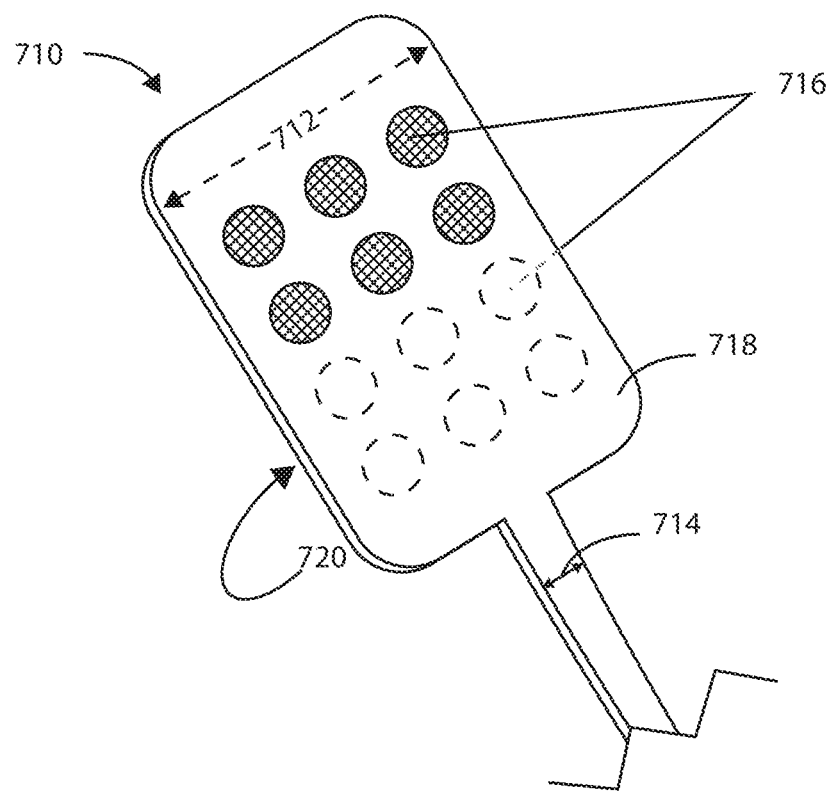
FIG. 8 is a schematic view of a portion of a lead in accordance with various embodiments herein.

Referring now to FIG. 8, the paddle 710 can include a first side 718 configured to face a cancerous tumor and a second side 720 opposite the first side 718. In some embodiments, the one or more electrodes 716 can be disposed on the first side 718. In some embodiments, the one or more electrodes 716 can be disposed on the second side 720, opposite the first side 718. In other embodiments, the one or more electrodes 716 can be disposed on both the first side 718 and the second side 720. The paddle 710 can have a width 712 that is greater than a width 714 of the lead body 704.

To provide a means to modulate the shape and position of the electric field about the site of a cancerous tumor, in some embodiments the one or more leads 702 can be configured to implement a switching mechanism to change which electrodes are currently in electrical communication with the proximal end 706 of the lead body 704.

The one or more leads 702 can be suitable for use in a method of treating a cancerous tumor, in accordance with the embodiments herein. The method of treating a cancerous tumor can include implanting one or more leads 702 within a patient, where the one or more leads 702 include a lead body 704 having a proximal end 706 and a distal end 708. The lead body 704 can define a lumen (not shown) and include a paddle 710 disposed at the distal end 708 of the lead body 704. As described above, the paddle 710 can have a width 712 that is greater than a width 714 of the lead body 704. There can be one or more electrodes 716 disposed on the paddle 710. There can be one or more electrical conductors (not shown) disposed within the lumen of the lead body 704 to provide electrical communication between the one or more electrodes 716 and the proximal end 706 of the lead body 704. The method of treating a cancerous tumor can also include the step of generating an electric field at the site of a cancerous tumor from the one or more electrodes 706.

Figure 9:
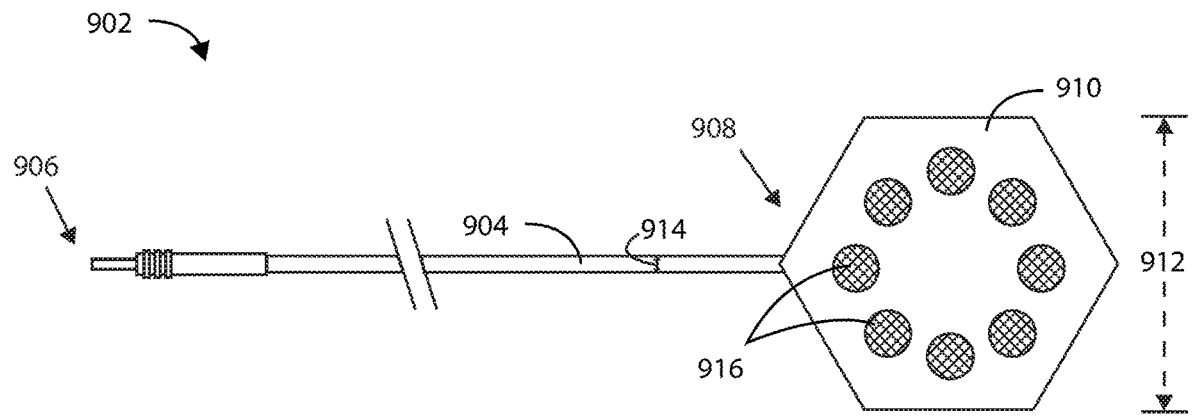
FIG. 9 is a schematic view of a lead in accordance with various embodiments herein.

Referring now to FIG. 9, a lead 902 is shown in accordance with various embodiments herein. The lead 902 can include a lead body 904 having a proximal end 906 and a distal end 908. The lead body 904 can include a patch 910 disposed at the distal end 908 of the lead body 904. The patch 910 can have a width 912 that is greater than the width 914 of the lead body 904. The patch 910 can be configured to be implanted within a subcutaneous space of a patient. Fixation of the patch 910 to an organ and/or tumor site can be achieved by a suture, staple, talon, glue, and the like. There can be one or more electrodes 916 disposed on the patch 910. There can also be one or more conductors (not shown) passing through the lead body 904 and providing electrical communication between the one or more electrodes 916 and the proximal end 906 of the lead body 904. In some embodiments, the patch 910 can be implanted subcutaneously.

In some embodiments, the lead 902 can include anywhere from 2 to 36 electrodes 916 disposed on the patch 910. In some embodiments, the one or more leads 902 can include anywhere from 2 to 50 electrodes 916 disposed on the patch 910. In some embodiments, the one or more leads 902 can include anywhere from 3 to 12 electrodes 916 disposed on the paddle 910. In some embodiments, the one or more leads 902 can include anywhere from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 electrodes 916 disposed on the patch 910. In some embodiments, the lead 902 can include one or more electrodes on a first side of patch 910 and one or more electrodes on a second side of patch 910. It will be appreciated that the one or more leads 902 can include any number of electrodes falling within a range, wherein any of the foregoing numbers can serve as the upper or lower bound of the range, provided that the upper bound is greater than the lower bound.

Figure 10:
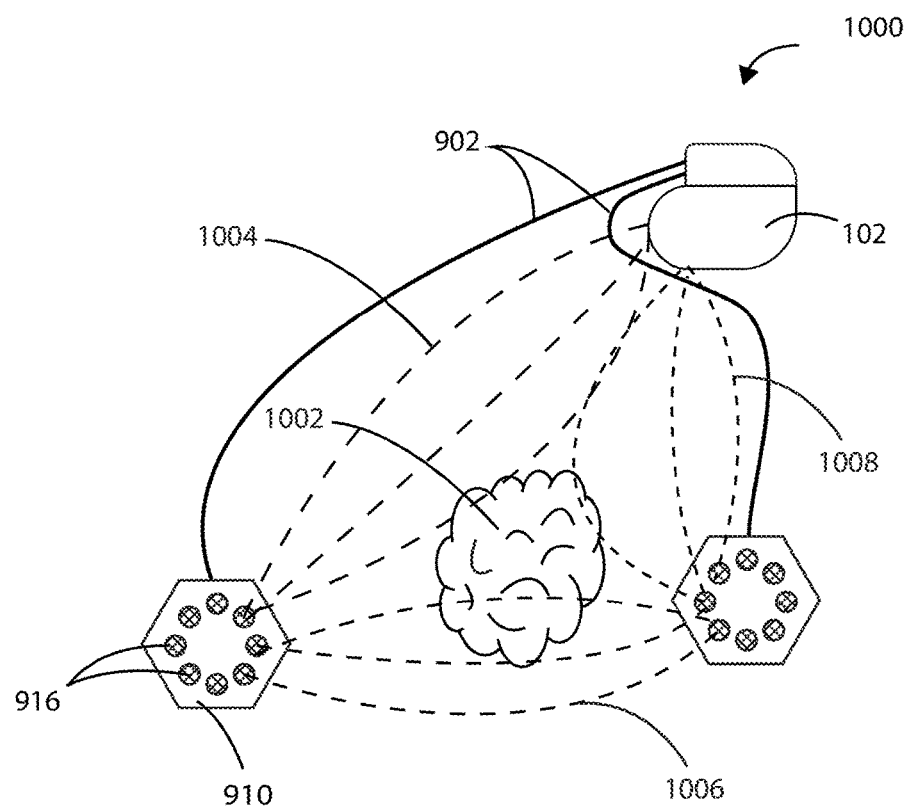
FIG. 10 is a schematic view of a medical device in accordance with various embodiments herein.

Referring now to FIG. 10, one or more leads 902 within cancer treatment system 1000 are shown in accordance with various embodiments herein. Cancer treatment system 1000 can include one or more leads 902 for implementing a cancer treatment for a cancerous tumor 1002.

Electric fields can be generated between any combinations of electrodes 916 disposed on patches 910 or housing 102. For example, near-field electric field 1006 can be generated between combinations of electrodes 916 disposed on two or more patches 910. In some embodiments, far-field electric fields 1004 and 1008 can be generated between any combinations of electrodes 916 disposed on one or more patches 910 and the housing 102 of a medical device. Many electric fields of various electric field strengths and shapes can be generated in cancer treatment system 1000 to provide spatial diversity to the electric fields about cancerous tumor 1002. It will be appreciated that electrodes used to generate near-field electric fields at or near the site of a cancerous tumor can provide high electric field density at the site of the tumor. In some embodiments, electrodes on a lead placed transvascularly near the site of a cancerous tumor can provide near-field field density to the cancerous tumor. It will also be appreciated that the electrodes and/or housing used to generate far-field electric fields can increase the spatial diversity of the electric field at the site of the tumor. In some embodiments, one or more subcutaneous patch electrodes can be used to increase the spatial diversity of the electric field at the site of the tumor. In some embodiments, mixtures of near-field and far-field leads can be used.

The one or more leads 902 can be suitable for use in a method for treating a cancerous tumor, in accordance with the embodiments herein. The method of treating a cancerous tumor can include implanting one or more patches 910 subcutaneously within a patient. The one or more patches 910 can include and one or more electrodes 916 disposed on the one or more patches. The one or more patches 910 can also include one or more electrical conductors (not shown) providing electrical communication with the one or more electrodes 916. The method of treating a cancerous tumor can also include generating one or more electric fields at or near the site of a cancerous tumor from the one or more electrodes 916.

Figure 11:
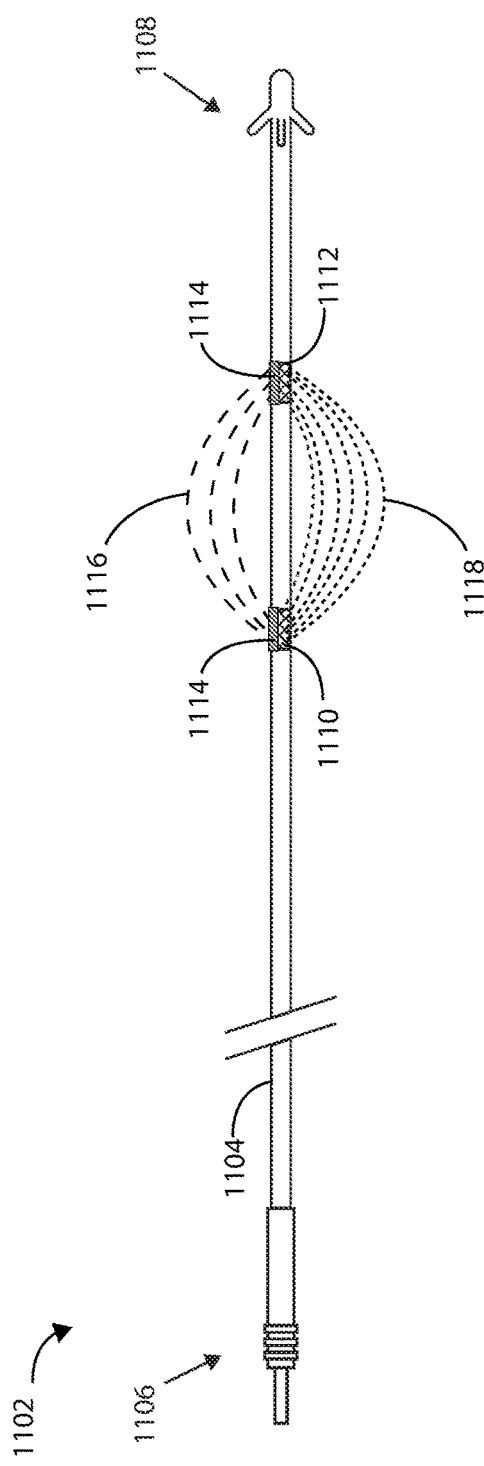
FIG. 11 is a schematic view of a lead in accordance with various embodiments herein.

Referring now to FIG. 11, a lead 1102 for use in a cancer treatment system is shown in accordance with the embodiments herein. The lead 1102 can include a lead body 1104 having a proximal end 1106 and a distal end 1108. The lead body 1104 can include one or more electrodes, such as electrodes 1110 and 1112. In some embodiments, the lead body 1104 can include two or more electrodes. The lead 1102 can also include one or more conductors (not shown) passing through the lead body 1104 to provide electrical communication between the one or more electrodes 1110 and 1112 and the proximal end 1106 of the lead body 1104. In some embodiments, the one or more electrodes can be oriented at different positions radially around the outside surface of the lead body 1104. In some embodiments, the one or more electrodes can be oriented at the same positions radially around the outside surface of the lead body 1104.

The electric field strength and direction can be manipulated in or near a tumor by coating all or part of the electrodes with an insulating material 1114. In some embodiments, the lead 1102 can include an insulating material 1114 disposed over all of one or more electrodes. In some embodiments, the lead 1102 can include an insulating material 1114 disposed over part of one or more electrodes. In some embodiments, the insulating material can be asymmetrically disposed over a portion of the one or more electrodes. In some embodiments, the electrodes can be disposed on the lead 1102 such that the electrodes are pointing in different directions. In other embodiments, the electrodes can be disposed on the lead 1102 such that the electrodes are pointing in the same direction.

The electric field strength can be affected by the placement and thickness of the insulating material 1114. For example, electric field 1116 shown between electrodes 1110 and 1112 can be weaker than electric field 1118 shown between electrodes 1110 and 1112 due to the insulating material 1114. Insulating material 1114 can be selected from various materials, including but not limited to electrically insulating polymers such as expanded polytetrafluoroethylene (ePTFE), polytetrafluoroethylene (ePTFE), polyethylene-co-tetrafluoroethene (ETFE), polyurethanes, silicones, poly(p-xylylene) polymers such as parylene polymers, polyether block amides such as PEBAX®, nylons, or derivatives thereof. In some embodiments, the electrodes can be insulated with various materials, including but not limited to hydrogels or fractal coatings such as iridium oxide, titanium oxide, tantalum pentoxide, other metal oxides, poly(p-xylylene) polymers such as Parylene, and the like.

Electrodes pointing in different directions can generate electric field vectors pointing in different directions, thus enabling the manipulation of the direction of the electric field. In some embodiments, two or more electrodes can be disposed on the same side of the lead 1102, while in other embodiments two or more electrodes can be disposed on opposite sides of the lead 1102. In some embodiments the two or more electrodes can be disposed 180 degrees apart. In yet other embodiments the two or more electrodes can be disposed 30 degrees, 45 degrees, 60 degrees, 90 degrees, 120 degrees, or 150 degrees apart as they are disposed radially around the outside surface of the lead body 1104.

Lead 1102 can be suitable for use in a method for treating a cancerous tumor, in accordance with the embodiments herein. The method of treating a cancerous tumor can include implanting a lead 1102 within a patient. The lead 1102 can include a lead body 1104 having a proximal end 1106 and a distal end 1108. The lead body 1104 can include one or more electrodes, such as electrodes 1110 and 1112. In some embodiments, the lead body 1104 can include two or more electrodes. The lead 1102 can also include one or more conductors (not shown) passing through the lead body 1104 to provide electrical communication between the one or more electrodes 1110 and 1112 and the proximal end 1106 of the lead body 1104. The lead 1102 can also include an insulating material 1114 disposed over a portion the one or more electrodes 1110 and 1112 asymmetrically around the diameter of the lead body. The method of treating a cancerous tumor can also include generating one or more electric fields at or near the site of a cancerous tumor from the two or more electrodes. In some embodiments, the method of treating a cancerous tumor can also include generating an electric field at or near the site of a cancerous tumor from three or more electrodes.

Figure 12:
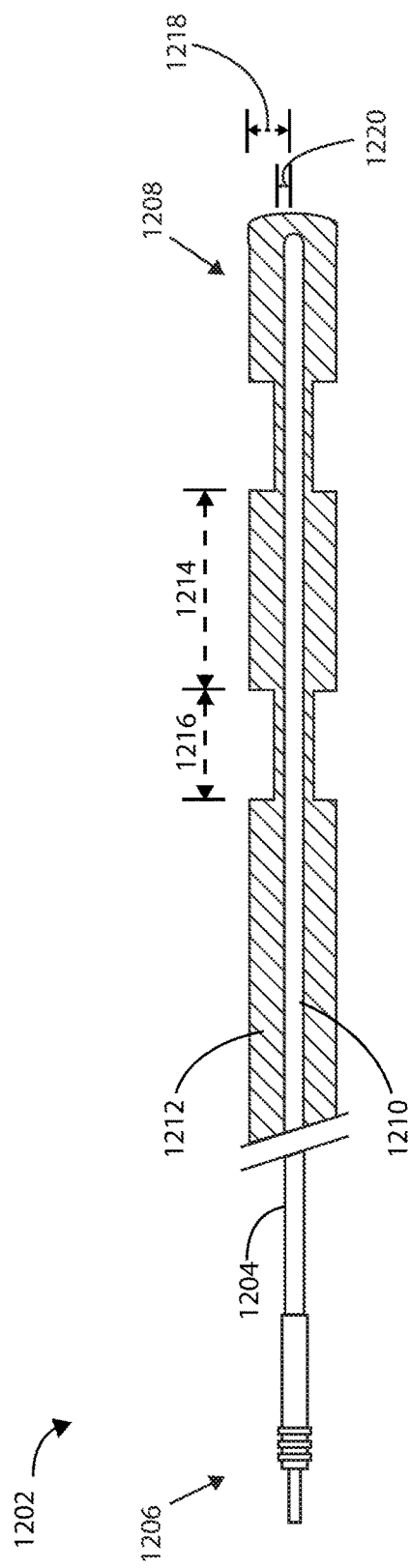
FIG. 12 is a schematic view of a lead in accordance with various embodiments herein.

Referring now to FIG. 12, a lead 1202 for use in a cancer treatment system is shown in accordance with the embodiments herein. The lead 1202 can include a lead body 1202 having a proximal end 1206 and a distal end 1208. The lead body 1202 can include one or more conductors 1210 disposed within the lead body 1202 to provide electrical communication. The lead body 1202 can also include an insulating material 1212 disposed over the one or more conductors 1210.

Modifying the thickness of the insulating material 1212 along conductor 1210 so that some regions are thicker and some regions are thinner can provide a mechanism to generate one or more electric fields having one or more electric field strengths in a specific region of interest. In some embodiments, optimal thicknesses for the insulating material 1212 can be less than 10 μm. In some embodiments, optimal thicknesses for the insulating material 1212 can be between about 1 μm to 5 μm. In some embodiments, optimal thicknesses for the insulating material 1212 can be between about 1 μm to 10 μm. In some embodiments, the optimal thicknesses for the insulating material 1212 can be anywhere from 1 μm, 2 μm, 3 μm, 4 μm, 5 μm, 6 μm, 7 μm, 8 μm, 9 μm, and 10 μm. It will be appreciated that the optimal thickness for the insulating material 1212 can fall within a range, wherein any of the foregoing thicknesses can serve as the upper or lower bound of the range, provided that the upper bound is greater than the lower bound.

The insulating material can include one or more first zones 1214 and one or more second zones 1216. The thickness 1218 of the insulating material 1212 over the first zones 1214 can be greater than the thickness 1220 of the insulating material 1212 over the second zones 1216. The second zones 1216 can function as electrodes to generate one or more electric fields at or near the site of a cancerous tumor.

In some embodiments, lead 1202 can be suitable for use in a method for treating a cancerous tumor, in accordance with the embodiments herein. The method of treating a cancerous tumor can include implanting a lead 1202 within a patient. The lead 1202 can include a lead body 1204 having a proximal end 1206 and a distal end 1208. The lead body 1204 can include one or more conductors 1210 disposed within the lead body 1204 to provide electrical communication. The lead body can also include an insulating material 1212 disposed over the one or more conductors 1210. The insulating material 1212 can include one or more first zones 1214 and one or more second zones 1216. The thickness 1218 of the insulating material 1212 over the first zones 1214 is greater than the thickness 1220 of the insulating material 1212 over the second zones 1216. The second zones can function as electrodes to generate one or more electric fields at or near the site of a cancerous tumor. The method of treating a cancerous tumor can also include generate one or more electric fields at or near the site of a cancerous tumor from the one or more electrodes.

Figure 13:
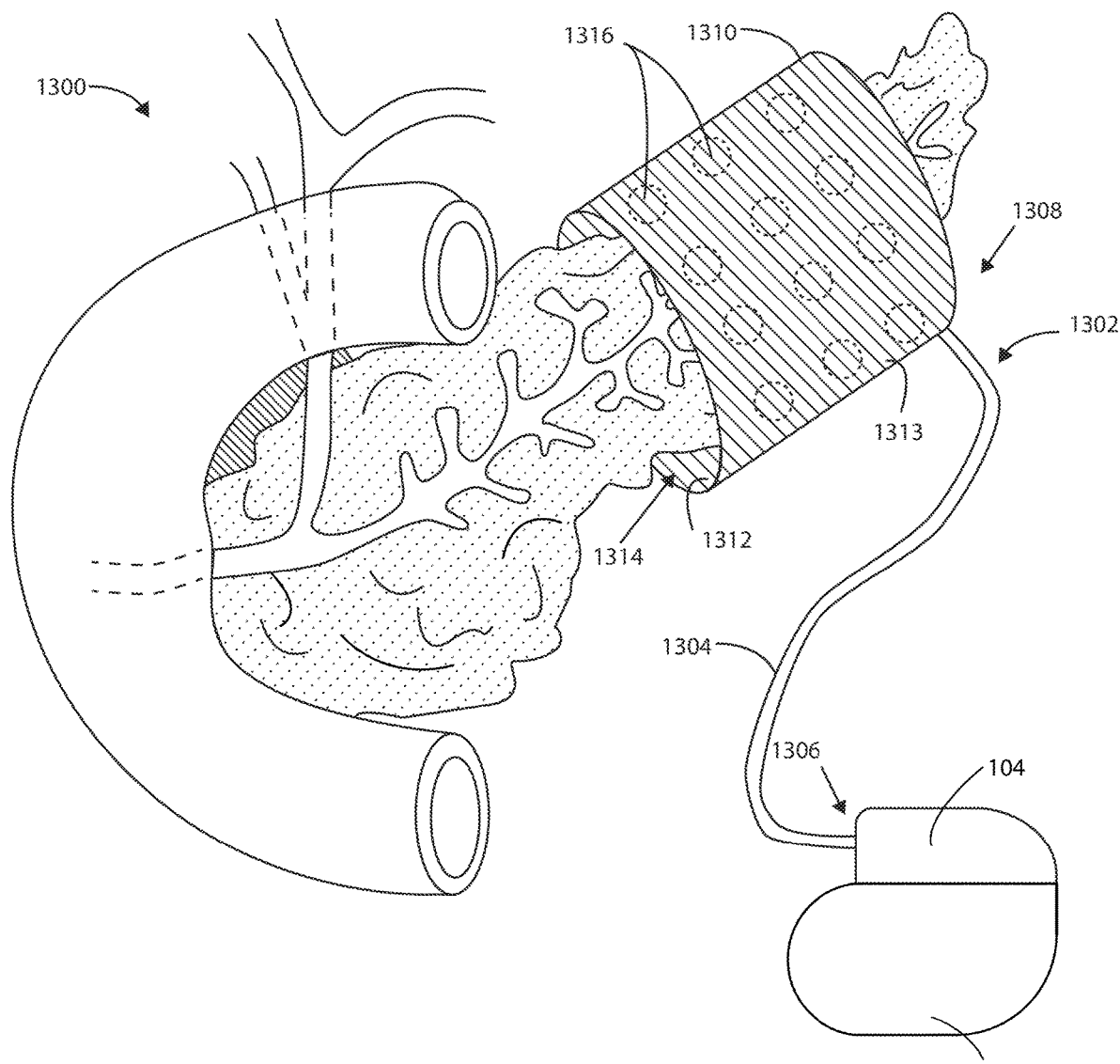
FIG. 13 is a schematic view of a medical device in accordance with various embodiments herein.

Referring now to FIG. 13, a cancer treatment system 1300 is shown in accordance with various embodiments herein. It will be appreciated that cancer treatment system 1300 is shown in the context of providing treatment to a site of a cancerous tumor in or near the pancreas, but cancer treatment system 1300 can be implanted at any suitable location within the body. The cancer treatment system 1300 can include a surgically implanted cuff 1310 that can be disposed around an organ containing a solid tumor, or the solid tumor itself.

Cancer treatment system 1300 can include one or more leads 1302 for delivering a cancer treatment. The leads 1302 can include a lead body 1304 having a proximal end 1306 and a distal end 1308. The lead body 1304 can define a lumen. The lead body 1304 can also include cuff 1310 disposed at the distal end 1308 of the lead body 1304. Fixation of the cuff 1310 to an organ and/or tumor site can be achieved by a suture, staple, talon, glue, and the like. The cuff 1310 can include an inner surface 1312 defining an inner cavity 1314. There can be two or more electrodes 1316 disposed on the cuff 1310 and arrayed on the inner surface 1312 of the cuff 1310. The lead body can also include one or more electrical conductors (not shown) disposed within the lumen of the lead body 1304 to provide electrical communication between the two or more electrodes 1316 and the proximal end 1306 of the lead body 1304. In some embodiments, one or more electrodes can be disposed on the outer surface 1313. In some embodiments, one or more electrodes can be disposed on the outer surface 1313 can act as counter electrodes to one or more electrodes disposed on the inner surface 1312.

In some embodiments, the one or more leads 1302 can include anywhere from 2 to 36 electrodes 1316 disposed on the cuff 1310. In some embodiments, the one or more leads 1302 can include anywhere from 2 to 50 electrodes 1316 disposed on the cuff 1310. In some embodiments, the one or more leads 1302 can include anywhere from 3 to 12 electrodes 1316 disposed on the cuff 1310. In some embodiments, the one or more leads 1302 can include anywhere from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 electrodes 1316 disposed on the cuff 1310. It will be appreciated that the one or more leads 1302 can include any number of electrodes falling within a range, wherein any of the foregoing numbers of electrodes can serve as the upper or lower bound of the range, provided that the upper bound is greater than the lower bound.

In some embodiments, the electrodes 1316 can be arranged in a grid pattern on the inner surface 1312 of the cuff 1310. In some embodiments, the electrodes 1316 can be arranged in a circular array on the inner surface 1312 of the cuff 1310. The electrodes 1316 can be field generating electrodes or field sensing electrodes. The electrodes 1316 can be disposed on the cuff 1310 such that each can be activated independently to generate an electric field of various shapes and sizes. The electrodes 1316 disposed on cuff 1310 can each be activated independently to sense and electric field.

To provide a means to modulate the shape and position of the electric field about the site of a cancerous tumor, in some embodiments the one or more leads 1302 can be configured to implement a switching mechanism to change which electrodes on cuff 1310 are currently in electrical communication with the proximal end 1306 of the lead body 1304. It will be appreciated that the switching mechanism is controlled by the electric field generating circuit, discussed above with respect to FIG. 3. Electric field generating circuit can be configured to switch the polarity of one or more electrodes in a multiple electrode array, of three or more electrodes, to change the field shape.

The cuff 1310 can be created from any number of biocompatible materials. In some embodiments, the cuff 1310 can be made from an elastomeric material. Elastomeric materials suitable for use herein can include, but not be limited to polymers such as expanded polytetrafluoroethylene (ePTFE), polytetrafluoroethylene (ePTFE), polyethylene-co-tetrafluoroethene (ETFE), polyurethanes, silicones, high-durometer silicones, poly(p-xylylene) polymers such as parylene polymers, polyether block amides such as PEBAX®, nylons, or derivatives thereof. Additionally, the elastomeric materials can be reinforced by materials such as shape-set metals including but not limited to nitinol, to provide additional structural support for clamping down on a tissue containing a cancerous tumor.

It will be appreciated that in some embodiments, the cuff 1310 can expand in diameter by at least 50% without structural failure. It will be appreciated that in other embodiments, the cuff 1310 can expand in diameter by at least 150% without structural failure. In some embodiments, the cuff 1310 can expand in diameter by at least 300% without structural failure. In some embodiments, the cuff 1310 can expand in diameter by 10%, 2%, 30%, 40%, 50%, 60%, 70%, 7%, 80%, 90%, 100%, 12%, 150%, 17%, 200%, 22%, 250%, 27%, 300%, 350%, 400%, 450%, or 500%. It will be appreciated that the cuff 1310 can expand in diameter by any percentage falling within a range of percentages, wherein any of the foregoing percentages can serve as the upper or lower bound of the range, provided that the upper bound is greater than the lower bound.

When implanted, it will be appreciated that cuff 1310 can conform to the shape of the underlying organ or tumor. In some embodiments, the cuff 1310 can include a slit such that it is not a contiguous cylinder. In some embodiments, the cuff 1320 can be reinforced with a shape set material such that it assumes a first elongated rectangular configuration prior to implant, and a second curled cylindrical configuration when implanted around the site of a cancerous tumor.

In some embodiments, the cuff 1310 can include a substrate with a plurality of apertures disposed therein. In some embodiments, the cuff can include an expandable woven substrate. Some non-limiting examples of woven substrate materials can include, but not be limited to aramid, nylons, urethanes, expanded polytetrafluoroethylene (ePTFE), polytetrafluoroethylene (ePTFE), polyethylene-co-tetrafluoroethene (ETFE), and the like. In some embodiments, the cuff 1310 can be a contiguous cylinder. Some additional examples of non-woven substrate materials can include those created with electrospin processes using polymers such as aramid, nylons, urethanes expanded polytetrafluoroethylene (ePTFE), polytetrafluoroethylene (ePTFE), polyethylene-co-tetrafluoroethene (ETFE), and the like.

Lead 1302 can be suitable for use in a method for treating a cancerous tumor, in accordance with the embodiments herein. The method of treating a cancerous tumor can include implanting a lead 1302 within a patient and fixing the cuff 1310 at the site of a cancerous tumor. The lead 1302 can include a lead body 1304 having a proximal end 1306 and a distal end 1308. The lead body can include a lumen and a cuff disposed at the distal end 1308 of the lead body 1304. The cuff 1310 can include an inner surface 1312 defining an inner cavity 1314. There can be two or more electrodes 1316 disposed on the cuff 1310 and arrayed on the inner surface 1312 of the cuff 1310. The lead body 1304 can also include one or more electrical conductors (not shown) disposed within the lumen of the lead body 1304 to provide electrical communication between the two or more electrodes 1316 and the proximal end 1308 of the lead body 1304. The method of treating a cancerous tumor can also include generating one or more electric fields at or near the site of to a cancerous tumor from the one or more electrodes.

Figure 14:
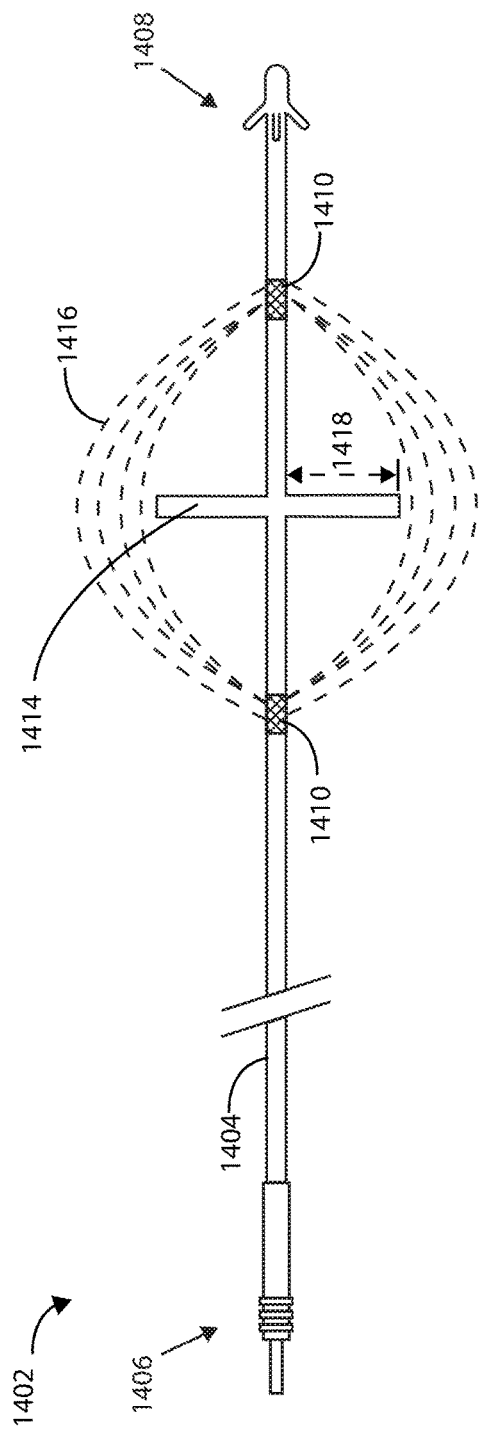
FIG. 14 is a schematic view of a lead in accordance with various embodiments herein.

Referring now to FIG. 14, a lead 1402 for use in a cancer treatment system is shown in accordance with the embodiments herein. The lead 1402 can include a lead body 1404 having a proximal end 1406 and a distal end 1408. The lead body 1404 can include at least two electrodes 1410. The lead body 1404 can also include one or more conductors (not shown) passing through the lead body 1404 to provide electrical communication between the at least two electrodes 1410 and the proximal end 1408 of the lead body 1404. The lead body 1404 can also include an insulating flange 1414 disposed circumferentially on an exterior surface of the lead body, the insulating flange 1414 can be made from an insulating material that can interrupt an ionic conduction path 1416 between the two electrodes 1410. In some embodiments without an insulating flange 1414, the direct electrical conduction path 1416 can be a straight-line ionic conduction path. In some embodiments with an insulating flange 1414, the direct ionic conduction path 1416 is a curved path.

In some embodiments, the insulating flange 1414 can be configured about lead 1402 to direct a high field density farther away from the surface of the lead than what would otherwise be found in a straight line path between two or more electrodes. The insulating flange 1414 can be selected from various materials, including but not limited to electrically insulating polymers such as expanded polytetrafluoroethylene (ePTFE), polyurethanes, silicones, and the like. In some embodiments, insulating flange 1414 can be flexible so as to facilitate ease of delivery through the vascular system. In some embodiments, upon delivery of the lead 1402 within the vascular system near the site of a cancerous tumor, insulating flange 1414 can expand within a vessel such that it acts to occlude the passage of blood to prevent low impedance electrical communication through the blood.

Insulating flange 1414 can extend about the circumference of lead 1402 by radial distance 1418. In some embodiments, radial distance 1418 can be identical all the way around the circumference of lead 1402. In other embodiments, radial distance 1418 can be a first radial distance about half of the circumference and a second radial distance about the opposite half of the circumference about the lead 1402. The radial distance 1418 can extend from the surface of lead 1402 by anywhere from 1 mm to 50 mm in length. It will be appreciated that the radial distance 1418 can be selected from a range of distances including 1 mm, 2 mm, 3 mm, 4 mm, 5 mm, 6 mm, 7 mm, 8 mm, 9, mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm.

Figure 15:
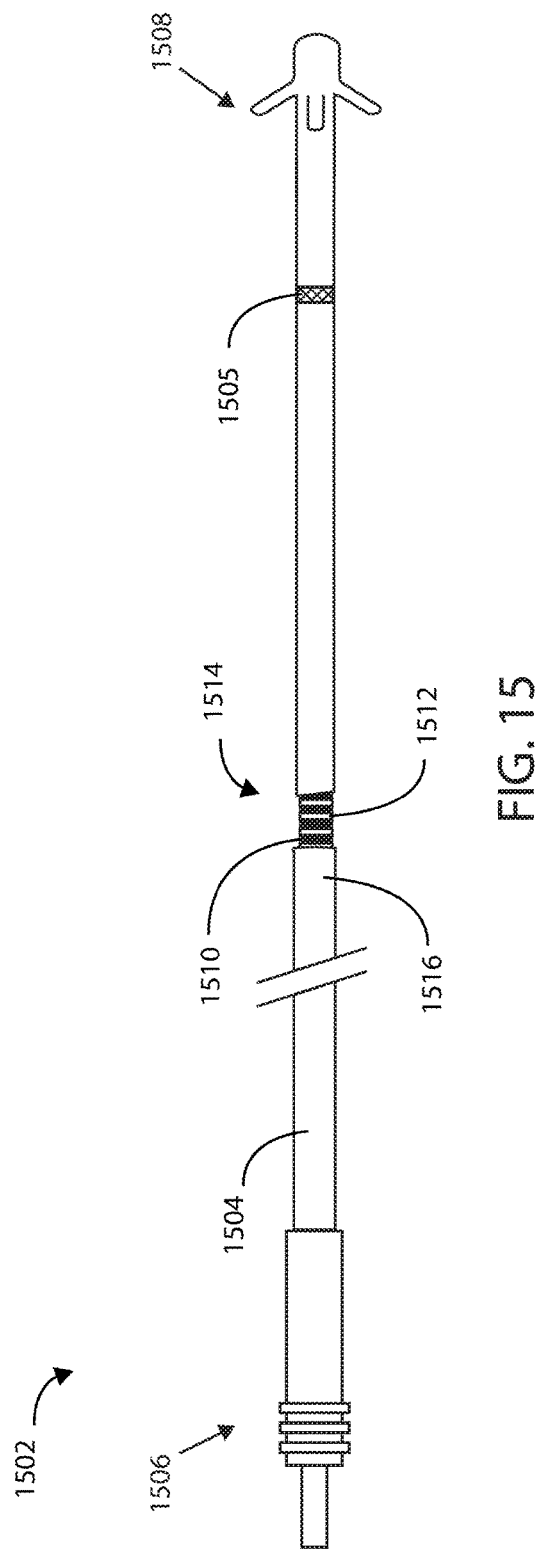
FIG. 15 is a schematic view of a lead in accordance with various embodiments herein.

Referring now to FIG. 15, a lead 1502 is shown in accordance with the embodiments herein. The lead 1502 can include a lead body 1504 having a proximal end 1506 and a distal end 1508. The lead body 1504 can include one or more electrodes, such as ring electrode 1505. The lead 1502 can include a conductor core that can be created from one or more sets of wound coils having one, two, three, four, five, or more individual coils wound about a common axis. The coil shown in FIG. 14 is a bifilar coil that includes two individual coils 1510 and 1512 wound about one another. In some embodiments the coil can be a trifilar coil. Insulating material 1516 is shown in a cut-away view, but it will be appreciated that the insulating material 1516 can cover the entire length of the lead 1502. In some embodiments, the insulating material 1516 has been cut away at locations 1514. In some embodiments, locations 1514 can serve as an electrode.

In some embodiments, it is useful to pair an electrode, such as an electrode 1514, distally with a counter electrode at or near the tumor in order to provide spatial diversity of the electric field. Multiple electrodes and counter electrodes placed near a tumor can provide high electric field density at the site of the tumor through use of near-field electrodes. Using the housing of the medical device and/or an electrode placed distal to the tumor can increase the spatial diversity of the electric field at the site of the tumor through use of far-field electrodes.

Leads and Electrodes

The leads described herein can be placed into the body near the site of a cancerous tumor using a number of techniques. Placement of one or more leads can include using techniques such as transvascular placement, tunneling into the subcutaneous space, and/or surgical placement. In some embodiments, the placement of one or more leads can include placement via one or more natural body orifices. The leads can be placed adjacent to or within a cancerous tumor. In some embodiments, multiple leads can be used near to or far from the cancerous tumor.

In some embodiments one or more leads described herein can be placed in the subcutaneous space. Electrodes on leads placed in the subcutaneous space can be used as the primary near-field generating electrode or as a far-field field generating electrode. In some embodiments, electrodes on leads placed in the subcutaneous space can be used as the primary near-field generating electrode or as a far-field field generating electrode in conjunction with the housing of a medical device. Likewise, one or more leads can be placed transvascularly to act as far-field field generating electrodes in conjunction with an electrode at or near the site of the cancerous tumor or in conjunction with the housing of a medical device.

The leads and electrodes described herein can include additional functional and structural features. In some embodiments, the leads can include those that are compatible with imaging and treatment techniques, including but not limited to MRI (magnetic resonance imaging), X-ray imaging, deep brain stimulation techniques, and/or radiation therapy. In some embodiments, the leads can include one or more conductor cores made from conducting materials. The conductor cores can be formed from conducting materials including metals and/or other conducting materials. Metals can include, but are not limited to, palladium, platinum, silver, gold, copper, aluminum, various alloys including stainless steel, nickel-cobalt alloys such as MP35N® and the like. In some embodiments, the conductor core can be a multifilar coil, including but not limited to a bifilar coil, a trifilar coil, and a quadfilar coil.

In some embodiments, electrodes can be disposed along the length of one or more leads as described herein. Suitable materials for use in the electrodes described herein can include metals such as palladium, to minimize coupling and artifact generation in magnetic fields. In some embodiments, electrodes can be made from other metals and/or other conducting materials. Metals can include, but are not limited to, palladium, platinum, platinum alloys such as platinum-iridium alloy, gold, copper, tantalum, titanium, various alloys including stainless steel, and the like. In some embodiments, electrodes can be in the form of wound coils that can provide an added benefit of increased surface area without compromising flexibility of the electrodes. In some embodiments, the implantable device housing can serve as an electrode.

The leads described herein can also include one or more electrodes disposed along the length of the lead. The leads can include two or more electrodes disposed along the length of the lead. In some embodiments, the electrodes can be tip electrodes found at the distal end of the lead. In other embodiments, the electrodes can be ring electrodes found along the lead but not at the tip of the lead. In some embodiments, the electrodes can be coil electrodes. In some embodiments, a ring or tip electrode can be positioned in or adjacent to a tumor or cancerous tissue and a coil electrode can be positioned farther from the tumor or cancerous tissue in order to help provide spatial diversity to the generated electric fields. In some embodiments, one or more electrodes can have a length along the lengthwise axis (e.g., proximal to distal axis) of about 0.5, 1, 1.5, 2, 3, 4, 5, 7.5, 10, 15, 20, 30, 40, 50, 75, 100 mm or more. In some embodiments, one or more of the electrodes can have a length falling within a range wherein any of the foregoing distances can serve as the upper or lower bound of the range, provided that the upper bound is greater than the lower bound.

The leads can be unipolar, bipolar, or multipolar. In some embodiments, a unipolar lead can include a lead that generates an electric field between one electrode and the housing of the medical device. In some embodiments, a bipolar lead can include a lead that can generate and electric field between two electrodes disposed along the lead, or between both electrodes and the housing of the medical device. In some embodiments, a multipolar lead can include a lead that can generate an electric field between the more than two electrodes disposed along the lead, between more than two electrodes and the housing of the medical device, or any number of combinations of configurations of electrodes and the housing of the medical device.

The electrodes suitable for use here can be made of conductive polymers such as carbon filled silicone, polyacetylene, polypyrrole, polyaniline, polytiophene, polyfuran, polyisoprene, polybutadiene, polyparaphenylene, and the like. In other embodiments, the electrodes can be insulated. In some embodiments, the insulation surrounding and electrode can include microporous insulators to prevent cellular apposition, yet still allow for current flow. Microporous insulators can be made from a number of the insulating materials described herein, including but not limited to polytetrafluoroethylene (ePTFE), polyethylene-co-tetrafluoroethene (ETFE), polyurethanes, silicones, poly(p-xylylene) polymers such as Parylene polymers, polyether block amides such as PEBAX®, nylons, or derivatives thereof. In some embodiments, the electrodes can be coated with various materials, including but not limited to hydrogels or fractal coatings such as iridium oxide, titanium oxide, tantalum pentoxide, other metal oxides, poly(p-xylylene) polymers such as Parylene, and the like.

A number of lead fixation techniques and configurations can be used in accordance with the embodiments herein. Some non-limiting examples of lead fixation techniques can include biocompatible glue fixation, talon fixation, helix coil fixation, passive centering of the lead in the vascular system, tine fixation within the localized vascular system, spiral bias fixation within the localized vascular system, compression fixation, suture sleeve fixation, and the like. In some examples, the leads embodied herein can be placed within the vascular system surrounding or adjacent to the site of the cancerous tumor. In other embodiments, the leads embodied herein can be place surgically at or within or surrounding the site of the cancerous tumor.

The leads suitable for use herein can also include one or more open lumens that run the entire longitudinal length of, or a select portion of the longitudinal length of the lead. In some embodiments, the open lumen can include an integrated biopsy apparatus suitable for obtaining biopsy samples from a cancerous tumor site on a periodic basis to monitor disease progression and/or regression. Leads having an open lumen can also be configured to include an integrated drug delivery lumen that can deliver one or more drugs, such as steroids or chemotherapy agents, to the site of the tumor in a single bolus or periodically via a metered pump. The leads can include one or more portals disposed along the length of the lead to provide an outlet for drug delivery at or near the site of a cancerous tumor.

In some embodiments a portion of the lead or the entire lead can include a drug eluting coating. In some embodiments, the drug eluting coating can include an anti-inflammatory agent, such as a steroid. In some embodiments, the steroid can be dexamethasone. In other embodiments, the drug eluting coating can include a chemotherapy agent. In some embodiments, the chemotherapy agent can include a taxane or derivatives thereof, including but not limited to paclitaxel, docetaxel, and the like. In other embodiments, the drug eluting coating can be configured to release additional classes of chemotherapy agents, including, but not limited to alkylating agents, plant alkaloids such as vinca alkaloids, cytotoxic antibiotics, topoisomerase inhibitors, and the like. In some embodiments, the drug eluting coating can be configured to release the drug from the coating in a time-release fashion.

The leads herein can adopt a number of shapes or configurations. In some embodiments, the leads can be linear and in other embodiments the leads can be circular. A circular lead may be a completely closed loop or it may be a semi-closed loop. In some embodiments, the lead can include a bendable core that can allow the lead to be shaped into many configurations, including but not limited to a U shape, an S shape, a spiral shape, a half circle, an oval, and the like.

In yet other examples, the leads suitable for use herein can include fluorimetric or magnetic markers that can assist the clinician in precise placement at or near the site of a cancerous tumor. The leads can also include integrated pH sensors for detecting the change in the pH at or near the cancerous tumor or other chemical sensors suitable for analyzing the concentration of a chemical analyte of interest.

Therapy Parameters

Successful treatment of cancerous tumors can depend on a number of variables, including electric field strength, frequency, cell heterogeneity, cell size, cancer cell type, tumor size, and location within the body. A variety of therapy parameters can be implemented using the medical devices described herein. One or more therapeutic parameter sets can be programmed into the memory of the medical devices and implemented by the control circuitry 306, shown in FIG. 3. Exemplary therapeutic parameter sets can include those that implement the following concepts: sweeping through a range of frequencies; stacking of one or more frequencies simultaneously; stepping through one or more frequencies sequentially; the spatial or temporal delivery of one or more electric fields; sweeping through a range of electric field strengths; applying an effective spinning electric field; modulating a voltage control mode or a current control mode; implementing one or more duty cycles; pulse width modulation; manipulation of the waveform shape and/or pulse sequence; and the occasional use of high frequency or high electric fields strength pulses.

The therapeutic parameter sets can be programmed into a medical device to operate autonomously, or they can be queried and manipulated by the patient or a clinician using an external computation device such as a programmer, a home-based unit, and/or a mobile unit (e.g. a cellular phone, personal computer, smart phone, tablet computer, and the like). In other embodiments, the therapeutic parameter sets can be wirelessly communicated to the medical device from an external computation device. Frequencies and/or electric field strengths suitable for use in any of the therapeutic parameter sets herein are discussed above with respect to electric field generating circuit 320. In some embodiments, one or more therapeutic parameter sets can be implemented simultaneously. In other embodiments, one or more therapeutic parameter sets can be implemented in an alternating fashion.

Figure 16:
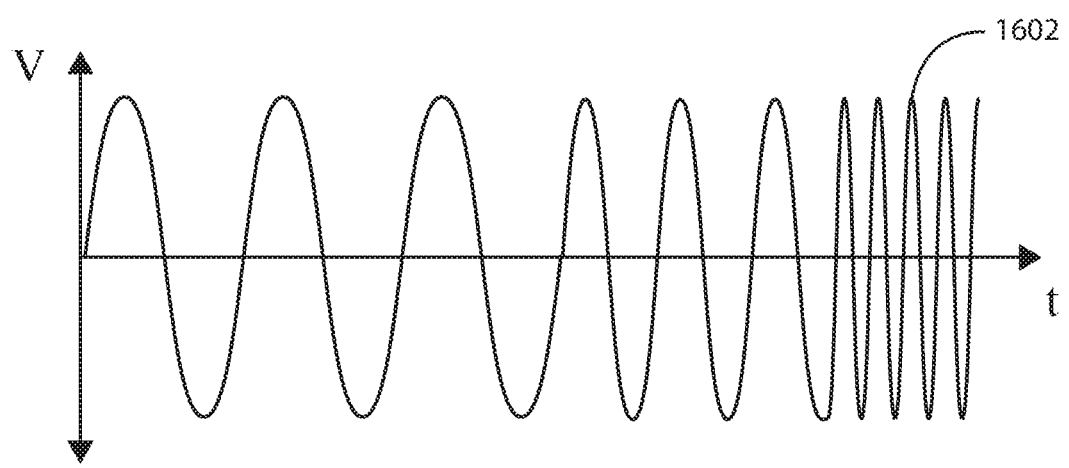
FIG. 16 is a plot of an exemplary therapy parameter in accordance with various embodiments herein.

Referring now to FIG. 16, exemplary plot 1602 shows an example of sweeping through a range of frequencies at the site of a cancerous tumor. Plot 1602 shows an alternating electric field, where the frequency is increased over time as the therapy is applied to the cancerous tumor. In some embodiments, a frequency sweep can include alternating between a first frequency sweep covering a range of about 100 kHz to 300 kHz and a second frequency sweep covering a range about 200 kHz to 500 kHz. It will be appreciated that sweeping through a first and second frequency range as described can be performed indefinitely throughout the course of the therapy.

Electric Field Generators

The medical devices embodied herein can include electric field generators particularly suited for therapeutic and diagnostic techniques used during the course of treatment for a cancerous tumor. In some embodiments, the electric field generators suitable for use herein can include those that have been treated by radiation hardening to make the components resistant to the damaging effects of radiation therapy treatments often prescribed as a main line treatment for cancerous tumors. Electric field generators can include components such as those described in reference to FIGS. 3 and 5 above.

Electric field generators embodied herein can be programmed with any number of therapeutic parameter sets as described. The electric field generators can be programmed prior to implant, or they can be programmed by a clinician using an external computation device such as a programmer, a home-based unit, and/or a mobile unit (e.g. a cellular phone, personal computer, smart phone, tablet computer, and the like). In some embodiments, therapy parameters can be delivered to the electric field generator via a telemetry circuit. In some embodiments, the electric field generator can include a recharge circuit communicatively coupled to a receiver coil to facilitate transcutaneous recharging of the medical device. In some embodiments, the electric field generator can communicate wirelessly between the receiver coil and an external charging device.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A lead for a cancer treatment system comprising:
   a lead body having a proximal end and a distal end, the lead body having a lumen with a cuff disposed at the distal end of the lead body, the lead body comprising one or more conductors disposed within the lead body and providing electrical communication; and
   an insulating material disposed circumferentially about and along the lead body over the one or more conductors;
   wherein the lead body comprises one or more first zones and one or more second zones, wherein the insulating material disposed over the one or more conductors in the first zones is thicker than the insulating material disposed over the one or more conductors in the second zones;
   wherein the second zones comprise at least a portion of the one or more conductors and at least a portion of the insulating material to form an electric field generating electrode configured to generate one or more therapeutic electric fields at or near a site of a cancerous tumor;

wherein the portion of the insulating material disposed about the one or more conductors in the second zones is configured to manipulate a strength of the one or more therapeutic electric fields generated by the electric field generating electrodes within the second zones;

the second zones having a stronger electric field than the first zones; and wherein the cuff is reinforced with a shape set material such that the cuff is in a first elongate rectangular configuration prior to implantation and a second curled cylindrical configuration when implanted around the site of the cancerous tumor;

wherein the cuff comprises two or more cuff electrodes disposed on the cuff, wherein each of the two or more cuff electrodes is activated independently; and wherein the cuff expands in diameter by at least 50% without structural failure.

2. The lead of claim 1, further comprising an insulating flange disposed circumferentially on an exterior surface of the lead body, the insulating flange comprising an insulating material and configured to interrupt a direct electrical conduction path between a second zone and a different second zone, wherein the second zone and the different second zone function as electrodes.

3. The lead of claim 2, wherein the direct electrical conduction path is a straight-line electrical conduction path.

4. The lead of claim 1, wherein at a site of each second zone, the insulating material is disposed asymmetrically in thickness around a diameter of the lead body.

5. The lead of claim 1, wherein the thickness of the insulating material over the one or more second zones is less than 10 µm.

6. The lead of claim 1, wherein the thickness of the insulating material over the one or more first zones is less than 10 µm.

7. The lead of claim 1, wherein the insulating material over the one or more first zones is different than the insulating material over the one or more second zones.

8. The lead of claim 1, wherein the insulating material is selected from one or more of expanded polytetrafluoroethylene (ePTFE), polytetrafluoroethylene (PTFE), polyethylene-co-tetrafluoroethene (ETFE), polyurethane, silicone, poly (p-xylylene) polymer, polyether block amide, nylon, iridium oxide, titanium oxide, and tantalum pentoxide.

9. The lead of claim 1, wherein the shape set material is nitinol.

10. The lead of claim 1, wherein the lead is configured to implement a switching mechanism to change which of the one or more cuff electrodes are in electrical communication with the lead.

11. A method of treating a cancerous tumor comprising:
implanting a lead within a patient, the lead comprising
a lead body having a proximal end and a distal end, the lead body comprising
one or more conductors disposed within the lead body and providing electrical communication;

an insulating material disposed circumferentially about and along the lead body over the one or more conductors, wherein the lead body comprises one or more first zones and one or more second zones, and wherein the insulating material over the one or more conductors in the first zones is thicker than the insulating material disposed over the one or more conductors in the second zones, each second zone comprising at least a portion of the one or more conductors and at least a portion of the insulating material to form an electric field generating electrode configured to generate one or more therapeutic electric fields at or near the site of a cancerous tumor; and a solid insulating flange disposed continuously circumferentially on an exterior surface of the lead body, wherein the solid insulating flange comprises a radial distance greater than its width, and wherein the solid insulating flange has a first segment having a first radial distance and a second segment having a second radial distance, such that the insulating flange is not radially symmetric in cross-section;

generating one or more therapeutic electric fields at or near the site of a cancerous tumor from the one or more electric field generating electrodes; and wherein the portion of the insulating material disposed about the one or more conductors in the second zones is configured to manipulate a strength of the one or more therapeutic electric fields generated by the electric field generating electrodes within the second zones; and the second zones having a stronger electric field than the first zones.

12. The method of claim 11, wherein at least one second zone comprises a coiled electrode in electrical communication with at least one of the one or more conductors.

13. The method of claim 12, wherein the coiled electrode is implanted subcutaneously.

14. The method of claim 11, wherein at a site of each second zone, the insulating material is disposed asymmetrically in thickness around a diameter of the lead body.

15. The method of claim 14, the one or more therapeutic electric fields comprising applied electric field strengths selected from a range of between 1 V/cm to 10 V/cm.

16. The method of claim 11, the one or more therapeutic electric fields delivered at one or more frequencies selected from a range of between 100 kHz to 300 kHz.

17. The method of claim 11, wherein the one or more therapeutic electric fields are generated using currents ranging from 20 mAmp to 500 mAmp.

18. The method of claim 11, wherein the therapeutic electric field is delivered to a site of a cancerous tumor along more than one vector.

19. The method of claim 18, wherein the therapeutic electric field is delivered to a site of a cancerous tumor along at least two vectors, wherein the vectors are disposed at an angle with respect to one another of at least 10 degrees.

* * * * *